(12) United States Patent
Kobie et al.

(10) Patent No.: US 12,421,301 B2
(45) Date of Patent: Sep. 23, 2025

(54) ANTI-INFLUENZA NEURAMINIDASE MONOCLONAL ANTIBODIES AND USES THEREOF

(71) Applicant: University of Rochester, Rochester, NY (US)

(72) Inventors: James J. Kobie, Rochester, NY (US); Luis Martinez-Sobrido, Rochester, NY (US); Michael Piepenbrink, Rochester, NY (US); Aitor Nogales, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 18/596,217

(22) Filed: Mar. 5, 2024

(65) Prior Publication Data
US 2024/0254205 A1 Aug. 1, 2024

Related U.S. Application Data

(62) Division of application No. 17/049,400, filed as application No. PCT/US2019/030383 on May 2, 2019, now Pat. No. 11,958,895.

(60) Provisional application No. 62/666,180, filed on May 3, 2018.

(51) Int. Cl.
| | |
|---|---|
| *C07K 16/00* | (2006.01) |
| *A61K 39/00* | (2006.01) |
| *A61K 39/42* | (2006.01) |
| *A61P 31/16* | (2006.01) |
| *C07K 16/10* | (2006.01) |

(52) U.S. Cl.
CPC .......... *C07K 16/1018* (2013.01); *A61K 39/42* (2013.01); *A61P 31/16* (2018.01); *A61K 2039/505* (2013.01); *C07K 2317/21* (2013.01); *C07K 2317/52* (2013.01); *C07K 2317/76* (2013.01)

(58) Field of Classification Search
None
See application file for complete search history.

(56) References Cited

FOREIGN PATENT DOCUMENTS

| | | |
|---|---|---|
| WO | 2016124682 A1 | 8/2016 |
| WO | 2017148889 A1 | 9/2017 |

OTHER PUBLICATIONS

Paul, Fundamental Immunology, 3rd Edition, 1993, pp. 292-295.*
Pascalis et al, Journal of Immunology, 2002, vol. 169, pp. 3076-3084.*
Casset et al (Biochemical and Biophysical Research Communications, 2003, vol. 307, pp. 198-205.*
Holm et al, Molecular Immunology, 2007, vol. 44, pp. 1075-1084.*
Wohlbold, T. J. et al., "Broadly Protective Murine Monoclonal Antibodies against Influenze B Virus Target Highly Conserved Neuraminidase Epitopes"; Nature Microbiology (2017); vol. 2; pp. 1415-1424.
Chen, Y. et al., "Influenza Inection in Humans Induces Broadly Cross-Reactive and Protective Neuraminidase-Reactive Atibodies"; Cell (2018); vol. 173; pp. 417-429.
Piepenbrink, M. S. et al., "Broad and Protective Influenza B. Virus Neuraminidase Antibodies in Humans after Vaccination and their Clonal Persistence as Plasma Cells"; MBIO (2019); vol. 10:2; pp. e00066-19.
International Search Report and Written Opinion issued on Jul. 30, 2019 for International Patent Application No. PCT/US19/30383 (15 pages).

* cited by examiner

*Primary Examiner* — Mark Halvorson
(74) *Attorney, Agent, or Firm* — Fox Rothschild LLP

(57) ABSTRACT

The present invention relates to broadly neutralizing anti-influenza monoclonal antibodies or antigen-binding fragments thereof. The present invention further relates to therapeutic uses of the isolated antibody or the antigen-binding fragment thereof.

16 Claims, 14 Drawing Sheets
Specification includes a Sequence Listing.

| mAb | Neutralization IC$_{50}$ (mAb ug/ml) | |
| --- | --- | --- |
| | B/Brisbane/60/2008 | B/Yamagata/16/88 |
| KPF2 | 0.252 | 0.346 |
| 1086F8 | 0.275 | 0.256 |
| 1086C12 | 0.960 | 2.472 |
| 1092E10 | 3.688 | 3.593 |
| 1122C6 | 1.075 | 0.807 |
| 1122C7 | 15.8 | 10.14 |

FIG. 2C

ANTI-INFLUENZA NEURAMINIDASE MONOCLONAL ANTIBODIES AND USES THEREOF

CROSS REFERENCE TO RELATED APPLICATION

This application is a Divisional of U.S. patent application Ser. No. 17/049,400 filed on Oct. 21, 2020, which is a U.S. National Phase of International Application No. PCT/US2019/030383, filed on May 2, 2019, which claims priority under 35 U.S.C. § 119(e) to U.S. Provisional Application No. 62/666,180 filed on May 3, 2018. The disclosures of which are hereby incorporated in their entirety.

GOVERNMENT INTERESTS

This invention was made with government support under 5R21AI116285 and NIH 272201400005C awarded by the National Institutes of Health. The government has certain rights in the invention.

REFERENCE TO AN ELECTRONIC SEQUENCE LISTING

The contents of the electronic sequence listing (SeqList-161118-00706.xml; Size: 86,379 bytes; and Date of Creation: Mar. 4, 2024) is herein incorporated by reference in its entirety.

FIELD OF THE INVENTION

This invention relates to broadly neutralizing anti-influenza neuraminidase monoclonal antibodies (mAbs) or antigen-binding fragments thereof. The present invention further relates to the therapeutic uses of the antibody or the antigen-binding fragment.

BACKGROUND OF THE INVENTION

Influenza, commonly known as "the flu", is an infectious disease caused by influenza virus. There are four types of influenza viruses: A, B, C and D. Human influenza A and B viruses cause seasonal epidemics of the disease. The first and most important step in preventing flu is to get an annual flu vaccination. Although a licensed influenza vaccine has been available for over seventy years, influenza infections still remain a major public health concern. Annually, in the United States influenza leads to ~15,000 deaths and ~300,000 hospitalizations, with about 3 to 5 million severe cases and 200,000 to 500,000 deaths per year globally (Girard M P, et al. 2005. Vaccine 23:5708-5724; Nogales A, et al. 2016. Int J Mol Sci 18; Dushoff J, et al. 2006. Am J Epidemiol 163:181-187; Doshi P. 2008. Am J Public Health 98:939-945; and Thompson W W, et al. 2009. Am J Public Health 99 Suppl 2:S225-230). In addition, the financial burden in the US averages more than 80 billion dollars annually, because of hospital costs or missed school or workdays (Molinari N A, et al. 2007. Vaccine 25:5086-5096; Gasparini R, et al. 2012. Hum Vaccin Immunother 8:21-28; and Keech M, et al. 2008. Pharmacoeconomics 26:911-924). There is a need for new vaccine strategies and therapeutics that confer broad protection against diverse influenza strains.

SUMMARY OF INVENTION

This invention addresses the need by providing broadly neutralizing anti-influenza neuraminidase monoclonal antibodies or antigen-binding fragments thereof.

In one aspect, the invention provides an isolated antibody or antigen-binding fragment thereof that specifically binds to a neuraminidase of influenza virus, comprising: (i) a heavy chain variable region (HCDR) that comprises HCDR1, HCDR2, and HCDR3 comprising the respective sequences of a HCDR set selected from the group consisting of SEQ ID NOs: 3-5, SEQ ID NOs: 11-13, SEQ ID NOs: 19-21, SEQ ID NOs: 27-29, SEQ ID NOs: 35-37, SEQ ID NOs: 43-45, SEQ ID NOs: 51-53, SEQ ID NOs: 59-61, SEQ ID NOs: 67-69, and (ii) a light chain variable region (LCDR) that comprises LCDR1, LCDR2 and LCDR3 comprising the respective sequences of a LCDR set selected from the group consisting of SEQ ID NOs: 6-8, SEQ ID NOs: 14-16, SEQ ID NOs: 22-24, SEQ ID NOs: 30-32, SEQ ID NOs: 38-40, SEQ ID NOs: 46-48, SEQ ID NOs: 54-56, SEQ ID NOs: 62-64, and SEQ ID NOs: 70-72. In some embodiments, the heavy chain variable region can comprise a sequence selected from the group consisting of SEQ ID NOs: 1, 9, 17, 25, 33, 41, 49, 57, and 65, and the light chain variable region can comprise a sequence selected from the group consisting of SEQ ID NOs: 2, 10, 18, 26, 34, 42, 50, 58, and 66. In one example, the heavy chain variable region comprises the sequences of SEQ ID NOs: 27-29, and the light chain variable region comprises the sequences of SEQ ID NOs: 30-32.

Further provided is an isolated antibody or the antigen-binding fragment thereof that competes for binding to a neuraminidase of influenza virus in a cross-blocking assay with the antibody or the antigen-binding fragment thereof described above.

The above-described antibody or antigen-binding fragment can include a variant Fc constant region. The isolated antibody or the antigen-binding fragment can be a chimeric antibody, a humanized antibody, or a human antibody. The antibody or fragment can be conjugated to a therapeutic agent, a polymer, a detectable label, or an enzyme. Examples of the polymer include polyethylene glycol (PEG). Examples of the therapeutic agent include a cytotoxic agent.

In a second aspect, the invention provides an isolated nucleic acid encoding one or more of the CDRs, the heavy or light chain variable region, or antigen-binding portion, of any one of above-described antibodies or antigen-binding fragments. The nucleic acid can be used to express a polypeptide having one or more sets of the HCDRs or LCDRS, a chain of the antibody or antigen-binding fragment, or the antibody or fragment described above. For this purpose, one can operatively link the nucleic acid to suitable regulatory sequences to generate an expression vector. Accordingly, within the scope of this invention are a cultured host cell comprising the vector and a method for producing a polypeptide, an antibody, or antigen-binding portion thereof. The method includes: obtaining a cultured host cell comprising a vector comprising a nucleic acid sequence encoding one or more of the above mentioned CDRs, polypeptide, a heavy chain variable region or a light chain variable region of the antibody or antigen binding portion thereof as described above; culturing the cell in a medium under conditions permitting expression of a polypeptide encoded by the vector and assembling of an antibody or fragment thereof, and purifying the antibody or fragment from the cultured cell or the medium of the cell.

The antibody or fragment described above can be used in a method of neutralizing influenza virus or a method of treating, preventing or controlling an influenza virus infection. The method includes administering to a subject in need thereof a therapeutically effective amount of the antibody or fragment. Accordingly, the invention also provides a pharmaceutical composition comprising (i) the antibody or an antigen-binding fragment thereof, and (ii) a pharmaceutically acceptable carrier.

The details of one or more embodiments of the invention are set forth in the description below. Other features, objectives, and advantages of the invention will be apparent from the description and from the claims.

BRIEF DESCRIPTION OF THE DRAWINGS

FIGS. 2A, 2B, and 2C are diagrams and a table showing that N2 and NB hmAbs exhibit in vitro neutralizing activity. Madin-Darby canine kidney (MDCK) cells were infected with 100 plaque-forming unit (PFU) of indicated virus and then 1 h later hmAb dilutions were added and cultures incubated in quadruplicates for 48-60 h. Viral infection was quantitated by fluorescence detection or crystal violet staining (B/Yamagata/16/88).

(FIG. 5A) Increasing concentrations of hMAbs were tested for binding to the indicated NA proteins and IIV (FLUZONE) by ELISA. RU, relative units. (FIG. 5B) hMAbs were tested for avidity for NA proteins at 1 µg/ml in increasing concentrations of urea. (FIG. 5C) MDCK cells were mock infected (Mock) or infected (MOI of 0.1) with the indicated viruses and 17 h later were fixed and stained with 1 µg/ml of the NA-specific hMAbs and NA protein expression evaluated by Immunofluorescence assay (IFA). KPF1 is an H1-specific hMAb used as an internal control in this IFA. Bar, 100 µm. Designations used in the figure are as follows: Malaysia, B/Malaysia/2506/2004; Ohio, B/Ohio/01/2005; Brisbane, B/Brisbane/60/2008; Nevada, B/Nevada/03/2011; Yamagata, B/Yamagata/16/1988; Sydney, B/Sydney/507/2006; Wisconsin, B/Wisconsin/01/2010; Texas, B/Texas/06/2011; Lee, B/Lee/1940; pH1N1, A/California/4_NYICE_E3/2009.

(FIG. 6A) Fluorescence-based microneutralization assay. MDCK cells were infected with the indicated mCherry-expressing virus (B/Brisbane/60/2008 or reB/Yamagata/16/1988) and then incubated with 2-fold serial dilutions (starting concentration, 10 µg/ml) of the IBV NA-specific hMAbs. Virus neutralization was evaluated and quantified using a fluorescence microplate reader, and the percentage of infectivity was calculated using sigmoidal dose response curves. Mock-infected cells and viruses in the absence of hMAb were used as internal controls. Percentages of inhibition were normalized to infection in the absence of hMAb. Data show means of the results determined in triplicate. The 50% inhibitory concentrations ($IC_{50}$) values corresponding to the IBV NA hMAbs were determined using a fluorescence-based assay (FA) or a traditional viral neutralization assay (VN) and mCherry-expressing or wild-type (WT) viruses, respectively. (FIG. 6B) IBV NA-specific hMAbs inhibit NA enzymatic activity. B/Brisbane/60/2008 or B/Yamagata/16/1988 WT viruses were preincubated with 2-fold serial dilutions of the IBV NA-specific hMAbs, and NA activity was determined at 18 h postincubation on fetuin-coated plates. Data represent mean percentages of virus-alone NA activity from duplicate wells. The percentage of activity and the IC50 were calculated using sigmoidal dose response curves. (FIG. 6C) IBV NA hMAbs recognize IBV oseltamivir resistance mutations. MDCK cells were infected (MOI of 0.1) with the indicated WT and NA (E117A and H273Y) viruses, and hMAb binding (1 µg/ml) was evaluated by IFA. Bar, 100 µm.

DETAILED DESCRIPTION OF THE INVENTION

Figures 1A, 1B:
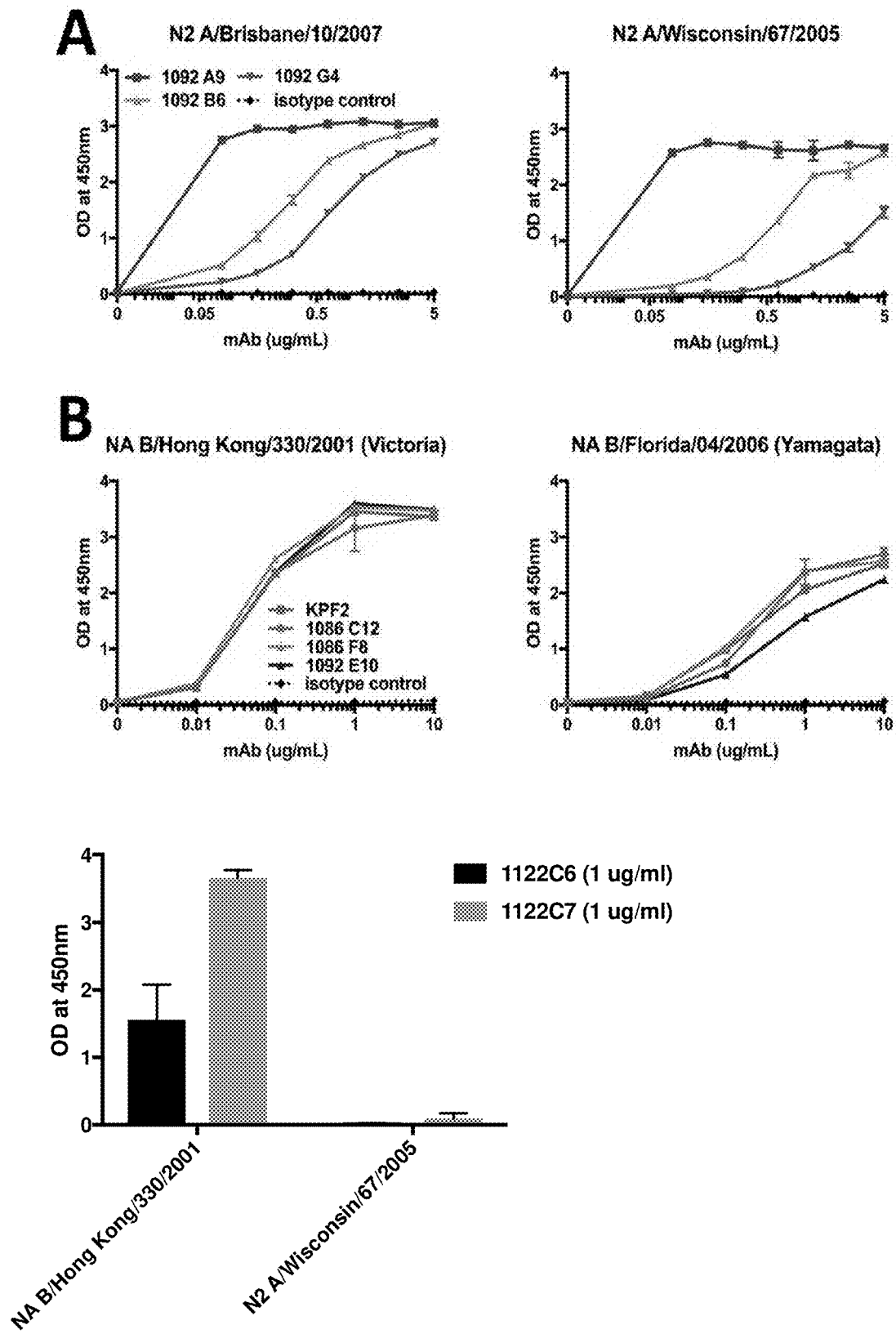
FIGS. 1A and 1B are a set of diagrams showing that influenza N2 and NB specific human monoclonal antibodies were isolated from peripheral blood plasmablasts. Plasmablasts (CD19+IgD-CD38+CD27++) were single cell sorted from peripheral blood 1 week following immunization and subjected to RT-PCR to amplify and clone the immunoglobulin heavy and light chain variable regions to obtain recombinant human monoclonal antibodies (hmAbs). HmAbs were screened by enzyme-linked immune-absorbent assay (ELISA) for targeting neuraminidase (NA) reactivity. Three N2-specific (A) and six NB specific hmAbs (B) were tested for binding to multiple NA proteins by ELISA.

This invention is based, at least in part, on unexpected broadly neutralizing anti-influenza activities of certain monoclonal antibodies or antigen-binding fragments thereof. These antibodies and antigen-binding fragments constitute a novel therapeutic strategy in protection from influenza infections.

Influenza's propensity for antigenic drift and shift, and to elicit predominantly strain specific antibodies (Abs) leaves humanity susceptible to waves of new strains with pandemic potential for which limited or no immunity may exist. Subsequently new clinical interventions are needed, particularly those with broad activity against diverse strains.

Although hemagglutinin (HA) specificity dominates the humoral response to seasonal inactivated influenza vaccines and infection, Abs targeting NA are also generated. NA-specific Abs are suggested to act primarily through inhibiting its enzymatic activity and preventing release of virus from infected cells. Relative to HA, there is substantially less diversity among NA from different influenza types and subtypes, suggesting it is a valuable target for inducing broad protective immunity.

Although immunogenic, the predominance of NA-specific antibodies is much lower than that of HA antibodies, probably because NA represents only one-fourth the amount of the HA on the virion surface. The yearly rate of mutation for NA is lower than for HA, while part of the enzymatic site (ILRTQESEC, SEQ ID NO: 73) remains conserved across influenza A virus (IAV) and IBV, making NA a potentially effective target for universal vaccine and therapeutic human monoclonal Ab (hMAb) development.

NA catalyzes the cleavage of terminal sialic acids from a large variety of glycoproteins, glycolipids, and oligosaccharides, with human isolates primarily exhibiting more-efficient cleavage of α2-3 linked sialic acid than α2-6 sialic acid. NA is important during the final stages of influenza virus infection, where it removes sialic acid from infected cell surfaces and newly formed virions, thus facilitating progeny virus release and spread of the infection to neighboring cells. NA can also promote penetration of the virus through the ciliated epithelium of the human airway by removing sialic acids on mucins, cilia, and the cellular glycocalyx. Thus, unlike antibodies against HA, antibodies against NA do not seem to be directly neutralizing influenza but rather prevent the spread of influenza viruses from infected cells by blocking the activity of the enzymatic site. Additionally, NA-specific Abs may also help clear virus through the engagement of the Fc region, thus mediating complement activation, antibody-dependent cellular cytotoxicity (ADCC), and antigen-dependent cellular phagocytosis (ADCP).

Accordingly, NA-specific Abs can prevent and treat influenza virus infection, using either active immunization with NA or passive immunization with NA-specific polyclonal or monoclonal Abs. The precise features of the human NA-specific B cell response to IIV, particularly the potential of IIV-induced NA-specific antibodies to directly mediate protection from influenza virus infection, remain poorly resolved.

To determine if humans generate NA-specific Abs with protective activity, this inversion examined plasmablasts from subjects that were immunized with the seasonal influenza inactivated vaccine, and isolated several NA-specific human monoclonal Abs, including those with potent in vitro viral neutralizing activity. One of the NA B-specific hmAbs, KPF2 recognized NA from both the Yamagata and Victoria lineages, and when administered prophylactically to mice resulted in sterilizing immunity. These results suggest seasonal influenza vaccine induces protective NA-specific mAbs in humans.

The results disclosed herein demonstrated that the seasonal IIV induces IBV NA-specific serum antibodies and B cells and isolated hMAbs that exhibit broad and potent in vitro and in vivo viral inhibition against IBV. The results also demonstrate the feasibility of targeting IBV NA with hMAbs for the therapeutic treatment of IBV infections.

Broadly antiviral hMAbs represent an excellent option for effective immunotherapeutics to prevent and treat influenza virus infection for which vaccine-induced immunity has not yet been achieved (representing lack of a vaccine [e.g., pandemic], a suboptimal vaccine, and/or an unvaccinated population) or where existing antiviral drugs are of limited efficacy. A few HA-specific hMAbs have been isolated that have antiviral activity against diverse influenza strains and are in clinical trials for the treatment of hospitalized patients and noncomplicated infections, highlighting the clinical feasibility and potential of influenza-specific hMABs. To inventors' knowledge, the antibodies disclosed herein represent the first IBV NA-specific hMAbs with broad antiviral activity to be described. The hMAbs described here, including but not limited to, 1086F8 and 1092D34, which suppressed virus to below detection, can be used prevent and treat influenza virus infection.

Antibodies

The invention disclosed herein involves broadly neutralizing anti-influenza monoclonal antibodies or antigen-binding fragments thereof. These antibodies refer to a class of neutralizing antibodies that neutralize multiple influenza virus strains. The antibodies are able to protect prophylactically and therapeutically a subject (e.g., a mouse as shown in the examples below) against a lethal challenge with an influenza virus, such as B/Brisbane/60/2008.

Listed below are amino acid sequences of the heavy chain (HC) variable regions and light chain (LC) variable regions of several exemplary antibodies, where the heavy chain CDR1-3 (HCDR1, HCDR2, and HCDR3) and light chain CDR1-3(LCDR1, LCDR2, and LCDR3) are in bold.

| Name | Sequence | SEQ ID NO: |
|---|---|---|
| | 1092A9 | |
| heavy chain variable region | EVQLLQSGGGLVQPGGSLRLSCAASGLTFSGYAMSWVRQVP GKGPECVSGIIASGGSTYFADSVKGRFTISRDNSKNTLDLE MNSLRAEDTAVYYCAQHTKSHYYSGMGVWGQGTTVTVSS | 1 |

-continued

| Name | Sequence | SEQ ID NO: |
|---|---|---|
| kappa light chain variable region | DIQMTQSPSSLSASVGDRVTITCQASQDISNYLNWYQQRPG KAPKLLIYDAANLETGVPSRFSGSGSATQFTFTISGLQPED FATYYCQQYDNLPLTFGGGTKVEIK | 2 |
| HCDR1 | GLTFSGYA | 3 |
| HCDR2 | IIASGGST | 4 |
| HCDR3 | AQHTKSHYYSGMGV | 5 |
| LCDR1 | QDISNY | 6 |
| LCDR2 | DAA | 7 |
| LCDR3 | QQYDNLPLT | 8 |

1092B6

| Name | Sequence | SEQ ID NO: |
|---|---|---|
| heavy chain variable region | QVQLVQSGAEVRKPGASVKVSCKVSRYNIIELSMDWVRQAP GKGLEWMGGIDPDDSERIYAQKLQGRVTMTEDTSTDTAYME LSGLRSEDTAIYYCAAARRPIRGEYHYALDVWGQGTAVTVS S | 9 |
| kappa light chain variable region | EIVLTQSPGTLSLSPGERATLSCRASQSVSSSYLGWYQQKP GQAPRLLIYRASSRATGIPHRFSGSGSGTEFTLTITRLEPE DFAVYYCHHYAKVFGQGTKVEIK | 10 |
| HCDR1 | RYNIIELS | 11 |
| HCDR2 | IDPDDSER | 12 |
| HCDR3 | AAARRPIRGEYHYALDV | 13 |
| LCDR1 | QSVSSSY | 14 |
| LCDR2 | RAS | 15 |
| LCDR3 | HHYAKV | 16 |

1092G4

| Name | Sequence | SEQ ID NO: |
|---|---|---|
| heavy chain variable region | QVQLVQSGADVKKPGASVKVSCKVSGYSLTELSMHWVRQAP GKGLEWMGGLDPDNGEIIYAQKFQGRVAMTEDTSTDTAYME LSSLRSEDTALYYCAAARRPIRGEYHYGMDVWGQGTTVTVS S | 17 |
| kappa light chain variable region | EIVLTQSPGTLSLSPGERATLSCRASQSLSSSYLAWYQQKS GQAPRLLIYGASSRATGVPDRFSGSGSGTDFTLTISRLEPE DFAVYYCQQYGKAFGQGTKVEIK | 18 |
| HCDR1 | GYSLTELS | 19 |
| HCDR2 | LDPDNGEI | 20 |
| HCDR3 | AAARRPIRGEYHYGMDV | 21 |
| LCDR1 | QSLSSSY | 22 |
| LCDR2 | GAS | 23 |
| LCDR3 | QQYGKA | 24 |

KPF2/1092D4

| Name | Sequence | SEQ ID NO: |
|---|---|---|
| heavy chain variable region | EVQLLESGGQLVQPGGSLRLSCAVSGFTFSRYAMYWVRQAP GKGLEWVSIISGDGGVTFYADSVKGRFTISRDNSKNTLFLQ MNSLRADDTAVYYCAKDNQDLDLWSGSYKGTFDDWGQGTLV TVSS | 25 |
| kappa light chain variable region | NFMLTQPHSVSGSPGKTVSISCTRSSGIIASNHVQWYQQRP GSAPTTVIFEDNQRPSGVPDRFSGSIDSSSNSASLTISGLK TEDEADYYCQSYDSSRYWVFGGGTKLTVL | 26 |

-continued

| Name | Sequence | SEQ ID NO: |
|---|---|---|
| HCDR1 | GFTFSRYA | 27 |
| HCDR2 | ISGDGGVT | 28 |
| HCDR3 | AKDNQDLDLWSGSYKGTFDD | 29 |
| LCDR1 | SGIIASNH | 30 |
| LCDR2 | EDN | 31 |
| LCDR3 | QSYDSSRYWV | 32 |

1086C12

| Name | Sequence | SEQ ID NO: |
|---|---|---|
| heavy chain variable region | VQLVESGGGVVQPGRSLRLSCVASGFSLSTYGMLWVRQAPG KGLVWVALISYEEGSNKKYADSVKGRFTISRDNSRNTLYLQ MSSLTSDDTGVYYCARDAGCDSVGYYPGRLWGQGTLVTVSS | 33 |
| kappa light chain variable region | QSVLTQPPSASGTPGQTVTISCSGTSSNIGSNFVYWYQQLP GTAPKLLIFRNNQRPSGVPDRFSGSKSGTSASLAVSGLRSE DEAEYYCAAWDDSLSGHLVFGGGTKLTVL | 34 |
| HCDR1 | GFSLSTYG | 35 |
| HCDR2 | ISYEEGSNK | 36 |
| HCDR3 | ARDAGCDSVGYYPGRL | 37 |
| LCDR1 | SSNIGSNF | 38 |
| LCDR2 | RNN | 39 |
| LCDR3 | AAWDDSLSGHLV | 40 |

1086F8

| Name | Sequence | SEQ ID NO: |
|---|---|---|
| heavy chain variable region | VQLVESGGGVVQPGRSLRLSCAASGFTFNTHPMHWVRQAPG KGLDWVAVISYDGSDEYYADSVKGRFTISRDDSKNTLYLQM NSLRPEDTAIYYCARDAGYDSRGYLPGPYWGQGTLVTVSS | 41 |
| kappa light chain variable region | QSVLTQPPSASGTPGQTVTISCSGSASTIGNNYVYWYQQLP GMAPKLLIFRDNQRPSVPDRFSGSKSGTSASLAIRGVRSD DEADYYCAAWDDSLSGHVMFGGXTKLTVL | 42 |
| HCDR1 | GFTFNTHP | 43 |
| HCDR2 | ISYDGSDE | 44 |
| HCDR3 | ARDAGYDSRGYLPGPY | 45 |
| LCDR1 | ASTIGNNY | 46 |
| LCDR2 | RDN | 47 |
| LCDR3 | AAWDDSLSGHVM | 48 |

1092E10

| Name | Sequence | SEQ ID NO: |
|---|---|---|
| heavy chain variable region | EVQLVESGGGSVKPGGSLRLSCAASGFTFTNSWMSWVRQAP GKGLEWVGRIKSKSDGGTTDYAAPVKGRFSISRDDSKSTLF LQMNSLKTEDTAVYYCSAAPFTESNGYKSWDYLYGMDVWGQ GTTVTVSS | 49 |
| kappa light chain variable region | SYELTQPPSVSVSPGQTATITCSGDKLGDKFASWYQQQPGQ SPVLVIYQHTKRPSGIPERFSGSISGSTATLTISGTQAVDE ADYYCQAWDSNSYVFGAGTKVTVL | 50 |
| HCDR1 | GFTFTNSW | 51 |
| HCDR2 | KSKSDGGTT | 52 |
| HCDR3 | SAAPFTESNGYKSWDYLYGMDV | 53 |
| LCDR1 | KLGDKF | 54 |

-continued

| Name | Sequence | SEQ ID NO: |
|---|---|---|
| LCDR2 | QHT | 55 |
| LCDR3 | QAWDSNSYV | 56 |

1122C6

| Name | Sequence | SEQ ID NO: |
|---|---|---|
| heavy chain variable region | QVQLQESGPGLVKPSETLSLTCTVSGGSISSYYWSWIRQPPGKAVEWIGYIFDGGSTDYNPSLKSRVAMSVDASENQFSLKLASVTAADTAVYYCARYRVSGNYYDTPWFDPWGQGLLVTVSS | 57 |
| kappa light chain variable region | SYELTQPPSLSASPGQTARITCSGDALPKQDVYWYQQKPGQAPLLVIYKDTERPSGIPERFSGSRSGTTVTLIISGVQAEDEADYYCQSAASSYGYVVFGGGTKLTVL | 58 |
| HCDR1 | GGSISSYY | 59 |
| HCDR2 | IFDGGST | 60 |
| HCDR3 | ARYRVSGNYYDTPWFDP | 61 |
| LCDR1 | ALPKQD | 62 |
| LCDR2 | KDT | 63 |
| LCDR3 | QSAASSYGYVV | 64 |

1122C7

| Name | Sequence | SEQ ID NO: |
|---|---|---|
| heavy chain variable region | EVQLLESGGQLVQPGGSLRLSCAVSGFTFSSYAMYWVRQSPGKGLEWVSIISGDGGVTFYADSVKGRFTISRDNSKNTLYLQMNSLRAEDTAVYYCAKDKQDLDLWSGSYKGTFDEWGQGTLVTVSS | 65 |
| kappa light chain variable region | NFMLTQPHSVSGSPGKTVSISCTRSSGIIASNYVQWYQQRPGSAPTTVIFEDNQRPSGVPDRFSGSIDSSSNSASLTISGLKTEDEADYYCQSYDSSRYWVFGGGTKLTVL | 66 |
| HCDR1 | GFTFSSYA | 67 |
| HCDR2 | ISGDGGVT | 68 |
| HCDR3 | AKDKQDLDLWSGSYKGTFDE | 69 |
| LCDR1 | SGIIASNY | 70 |
| LCDR2 | EDN | 71 |
| LCDR3 | QSYDSSRYWV | 72 |

Fragment

In certain embodiments, an antibody provided herein is an antibody fragment. Antibody fragments include, but are not limited to, Fab, Fab', Fab'-SH, F(ab')$_2$, Fv, and single-chain Fv (scFv) fragments, and other fragments described below, e.g., diabodies, triabodies tetrabodies, and single-domain antibodies. For a review of certain antibody fragments, see Hudson et al., Nat. Med. 9:129-134 (2003). For a review of scFv fragments, see, e.g., Pluckthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (DOMANTIS, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g., *E. coli* or phage), as described herein.

Chimeric and Humanized Antibodies

In certain embodiments, an antibody provided herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

Human Antibodies

In certain embodiments, an antibody provided herein is a human antibody. Human antibodies can be produced using various techniques known in the art or using techniques described herein. Human antibodies are described generally in van Dijk and van de Winkel, Curr. Opin. Pharmacol. 5: 368-74 (2001) and Lonberg, Curr. Opin. Immunol. 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENO-MOUSE technology; U.S. Pat. No. 5,770,429 describing HUMAB technology; U.S. Pat. No. 7,041,870 describing K-M MOUSE technology, and U.S. Patent Application Publication No. US 2007/0061900, describing VELOCI-MOUSE technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al., in Methods in Molecular Biology 178: 1-37 (O'Brien et al., ed., Human Press, Totowa, N.J., 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antibody fragments, either as scFv fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., EMBO J, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol., 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360. Antibodies or antibody fragments isolated from human antibody libraries are considered human antibodies or human antibody fragments herein.

Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen binding.

Substitution, Insertion, and Deletion Variants

In certain embodiments, antibody variants having one or more amino acid substitutions are provided. Sites of interest for substitutional mutagenesis include the HVRs and FRs. Conservative substitutions are defined herein. Amino acid substitutions may be introduced into an antibody of interest and the products screened for a desired activity, e.g., retained/improved antigen binding, decreased immunogenicity, or improved ADCC or CDC.

Accordingly, an antibody of the invention can comprise one or more conservative modifications of the CDRs, heavy chain variable region, or light variable regions described herein, e.g., SEQ ID NOs: 1-72. A conservative modification or functional equivalent of a peptide, polypeptide, or protein disclosed in this invention refers to a polypeptide derivative of the peptide, polypeptide, or protein, e.g., a protein having one or more point mutations, insertions, deletions, truncations, a fusion protein, or a combination thereof. It retains substantially the activity to of the parent peptide, polypeptide, or protein (such as those disclosed in this invention). In general, a conservative modification or functional equivalent is at least 60% (e.g., any number between 60% and 100%, inclusive, e.g., 60%, 70%, 75%, 80%, 85%, 90%, 95%, 96%, 97%, 98%, and 99%) identical to a parent (e.g., one of SEQ ID NOs: 1-72). Accordingly, within scope of this invention are heavy chain variable region or light variable regions having one or more point mutations, insertions, deletions, truncations, a fusion protein, or a combination thereof, as well as antibodies having the variant regions.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) J. Mol. Biol. 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used. (See www.ncbi.nlm.nih.gov).

As used herein, the term "conservative modifications" refers to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include:

amino acids with basic side chains (e.g., lysine, arginine, histidine),
acidic side chains (e.g., aspartic acid, glutamic acid),
uncharged polar side chains (e.g., glycine, asparagine, glutamine, serine, threonine, tyrosine, cysteine, tryptophan),
nonpolar side chains (e.g., alanine, valine, leucine, isoleucine, proline, phenylalanine, methionine),
beta-branched side chains (e.g., threonine, valine, isoleucine) and
aromatic side chains (e.g., tyrosine, phenylalanine, tryptophan, histidine).

Non-conservative substitutions will entail exchanging a member of one of these classes for another class.

An exemplary substitutional variant is an affinity matured antibody, which may be conveniently generated, e.g., using phage display-based affinity maturation techniques such as those described in e.g., Hoogenboom et al., in Methods in Molecular Biology 178:1-37 (O'Brien et al., ed., Human Press, Totowa, N.J., (2001). Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Glycosylation of the constant region on N297 may be prevented by mutating the N297 residue to another residue, e.g., N297A, and/or by mutating an adjacent amino acid, e.g., 298 to thereby reduce glycosylation on N297.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies described herein to thereby produce an antibody with altered glycosylation. For example, EP 1,176,195 by Hanai et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant Chinese Hamster Ovary cell line, Led 3 cells, with reduced ability to attach fucose to Asn(297)-linked carbohydrates, also resulting in hypofucosylation of antibodies expressed in that host cell (see also Shields, R. L. et al. (2002) J. Biol. Chem. 277:26733-26740). PCT Publication WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) Nat. Biotech. 17: 176-180).

Fc Region Variants

The variable regions of the antibody described herein can be linked (e.g., covalently linked or fused) to an Fc, e.g., an IgG1, IgG2, IgG3 or IgG4 Fc, which may be of any allotype or isoallotype, e.g., for IgG1: Glm, Glm1(a), Glm2(x), Glm3(f), Glm17(z); for IgG2: G2m, G2m23(n); for IgG3: G3m, G3m21(g1), G3m28(g5), G3 m11(b0), G3m5(b1), G3m13(b3), G3m14(b4), G3m10(b5), G3m15(s), G3m16 (t), G3m6(c3), G3m24(c5), G3m26(u), G3m27(v); and for K: Km, Km1, Km2, Km3 (see, e.g., Jefferies et al. (2009) mAbs 1:1). In certain embodiments, the antibodies variable regions described herein are linked to an Fc that binds to one or more activating Fc receptors (FcγI, FcγIIa or FcγIIIa), and thereby stimulate ADCC and may cause T cell depletion. In certain embodiments, the antibody variable regions described herein are linked to an Fc that causes depletion.

In certain embodiments, the antibody variable regions described herein may be linked to an Fc comprising one or more modification, typically to alter one or more functional properties of the antibody, such as serum half-life, complement fixation, Fc receptor binding, and/or antigen-dependent cellular cytotoxicity. Furthermore, an antibody described herein may be chemically modified (e.g., one or more chemical moieties can be attached to the antibody) or be modified to alter its glycosylation, to alter one or more functional properties of the antibody. The numbering of residues in the Fc region is that of the EU index of Kabat.

The Fc region encompasses domains derived from the constant region of an immunoglobulin, preferably a human immunoglobulin, including a fragment, analog, variant, mutant or derivative of the constant region. Suitable immunoglobulins include IgG1, IgG2, IgG3, IgG4, and other classes such as IgA, IgD, IgE and IgM, The constant region of an immunoglobulin is defined as a naturally-occurring or synthetically-produced polypeptide homologous to the immunoglobulin C-terminal region, and can include a CH1 domain, a hinge, a CH2 domain, a CH3 domain, or a CH4 domain, separately or in combination. In some embodiments, an antibody of this invention has an Fc region other than that of a wild type IgA1. The antibody can have an Fc region from that of IgG (e.g., IgG1, IgG2, IgG3, and IgG4) or other classes such as IgA2, IgD, IgE and IgM. The Fc can be a mutant form of IgA1.

The constant region of an immunoglobulin is responsible for many important antibody functions including Fc receptor (FcR) binding and complement fixation. There are five major classes of heavy chain constant region, classified as IgA, IgG, IgD, IgE, IgM, each with characteristic effector functions designated by isotype. For example, IgG is separated into four subclasses known as IgG1, IgG2, IgG3, and IgG4.

Ig molecules interact with multiple classes of cellular receptors. For example, IgG molecules interact with three classes of Fcγ receptors (FcγR) specific for the IgG class of antibody, namely FcγRI, FcγRII, and FcγRIIL. The important sequences for the binding of IgG to the FcγR receptors have been reported to be located in the CH2 and CH3 domains. The serum half-life of an antibody is influenced by the ability of that antibody to bind to an FcR.

In certain embodiments, the Fc region is a variant Fc region, e.g., an Fc sequence that has been modified (e.g., by amino acid substitution, deletion and/or insertion) relative to a parent Fc sequence (e.g., an unmodified Fc polypeptide that is subsequently modified to generate a variant), to provide desirable structural features and/or biological activity. For example, one may make modifications in the Fc region in order to generate an Fc variant that (a) has increased or decreased ADCC, (b) increased or decreased complement mediated cytotoxicity (CDC), (c) has increased or decreased affinity for Clq and/or (d) has increased or decreased affinity for an Fc receptor relative to the parent Fc. Such Fc region variants will generally comprise at least one amino acid modification in the Fc region. Combining amino acid modifications is thought to be particularly desirable. For example, the variant Fc region may include two, three, four, five, etc. substitutions therein, e.g., of the specific Fc region positions identified herein.

A variant Fc region may also comprise a sequence alteration wherein amino acids involved in disulfide bond formation are removed or replaced with other amino acids. Such removal may avoid reaction with other cysteine-containing proteins present in the host cell used to produce the antibodies described herein. Even when cysteine residues are removed, single chain Fc domains can still form a dimeric Fc domain that is held together non-covalently. In other embodiments, the Fc region may be modified to make it more compatible with a selected host cell. For example, one may remove the PA sequence near the N-terminus of a typical native Fc region, which may be recognized by a digestive enzyme in *E. coli* such as proline iminopeptidase. In other embodiments, one or more glycosylation sites within the Fc domain may be removed. Residues that are typically glycosylated (e.g., asparagine) may confer cytolytic response. Such residues may be deleted or substituted with unglycosylated residues (e.g., alanine). In other embodiments, sites involved in interaction with complement, such as the Clq binding site, may be removed from the Fc region. For example, one may delete or substitute the EKK sequence of human IgG1. In certain embodiments, sites that affect binding to Fc receptors may be removed, preferably sites other than salvage receptor binding sites. In other embodiments, an Fc region may be modified to remove an ADCC site. ADCC sites are known in the art; see, for example, Molec. Immunol. 29 (5): 633-9 (1992) with regard to ADCC sites in IgG1. Specific examples of variant Fc domains are disclosed for example, in WO 97/34631 and WO 96/32478.

In one embodiment, the hinge region of Fc is modified such that the number of cysteine residues in the hinge region is altered, e.g., increased or decreased. This approach is described further in U.S. Pat. No. 5,677,425 by Bodmer et al. The number of cysteine residues in the hinge region of Fc is altered to, for example, facilitate assembly of the light and heavy chains or to increase or decrease the stability of the antibody. In one embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the CI component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered Clq binding and/or reduced or abolished CDC. This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region may be modified to increase ADCC and/or to increase the affinity for an Fcγ receptor by modifying one or more amino acids at the following positions: 234, 235, 236, 238, 239, 240, 241, 243, 244, 245, 247, 248, 249, 252, 254, 255, 256, 258, 262, 263, 264, 265, 267, 268, 269, 270, 272, 276, 278, 280, 283, 285, 286, 289, 290, 292, 293, 294, 295, 296, 298, 299, 301, 303, 305, 307, 309, 312, 313, 315, 320, 322, 324, 325, 326, 327, 329, 330, 331, 332, 333, 334, 335, 337, 338, 340, 360, 373, 376, 378, 382, 388, 389, 398, 414, 416, 419, 430, 433, 434, 435, 436, 437, 438 or 439. Exemplary substitutions include 236A, 239D, 239E, 268D, 267E, 268E, 268F, 324T, 332D, and 332E. Exemplary variants include 239D/332E, 236A/332E, 236A/239D/332E, 268F/324T, 267E/268F, 267E/324T, and 267E/268F7324T. Other modifications for enhancing FcγR and complement interactions include but are not limited to substitutions 298A, 333A, 334A, 326A, 2471, 339D, 339Q, 280H, 290S, 298D, 298V, 243L, 292P, 300L, 396L, 3051, and 396L. These and other modifications are reviewed in Strohl, 2009, Current Opinion in Biotechnology 20:685-691.

Fc modifications that increase binding to an Fcγ receptor include amino acid modifications at any one or more of amino acid positions 238, 239, 248, 249, 252, 254, 255, 256, 258, 265, 267, 268, 269, 270, 272, 279, 280, 283, 285, 298, 289, 290, 292, 293, 294, 295, 296, 298, 301, 303, 305, 307, 312, 315, 324, 327, 329, 330, 335, 337, 3338, 340, 360, 373, 376, 379, 382, 388, 389, 398, 414, 416, 419, 430, 434, 435, 437, 438 or 439 of the Fc region, wherein the numbering of the residues in the Fc region is that of the EU index as in abat (WO00/42072).

Other Fc modifications that can be made to Fcs are those for reducing or ablating binding to FcγR and/or complement proteins, thereby reducing or ablating Fc-mediated effector functions such as ADCC, ADCP, and CDC. Exemplary modifications include but are not limited substitutions, insertions, and deletions at positions 234, 235, 236, 237, 267, 269, 325, and 328, wherein numbering is according to the EU index. Exemplary substitutions include but are not limited to 234G, 235G, 236R, 237K, 267R, 269R, 325L, and 328R, wherein numbering is according to the EU index. An Fc variant may comprise 236R/328R. Other modifications for reducing FcγR and complement interactions include substitutions 297A, 234A, 235A, 237A, 318A, 228P, 236E, 268Q, 309L, 330S, 331S, 220S, 226S, 229S, 238S, 233P, and 234V, as well as removal of the glycosylation at position 297 by mutational or enzymatic means or by production in organisms such as bacteria that do not glycosylate proteins. These and other modifications are reviewed in Strohl, 2009, Current Opinion in Biotechnology 20:685-691.

Optionally, the Fc region may comprise a non-naturally occurring amino acid residue at additional and/or alternative positions known to one skilled in the art (see, e.g., U.S. Pat. Nos. 5,624,821; 6,277,375; 6,737,056; 6,194,551; 7,317, 091; 8,101,720; WO00/42072; WO01/58957; WO02/06919; WO04/016750; WO04/029207; WO04/035752; WO04/074455; WO04/099249; WO04/063351; WO05/070963; WO05/040217, WO05/092925 and WO06/020114).

Fc variants that enhance affinity for an inhibitory receptor FcγRIIb may also be used. Such variants may provide an Fc fusion protein with immune-modulatory activities related to FcγRIIb cells, including for example B cells and monocytes. In one embodiment, the Fc variants provide selectively enhanced affinity to FcγRIIb relative to one or more activating receptors. Modifications for altering binding to FcγRIIb include one or more modifications at a position selected from the group consisting of 234, 235, 236, 237, 239, 266, 267, 268, 325, 326, 327, 328, and 332, according to the EU index. Exemplary substitutions for enhancing FcγRIIb affinity include but are not limited to 234D, 234E, 234F, 234W, 235D, 235F, 235R, 235Y, 236D, 236N, 237D, 237N, 239D, 239E, 266M, 267D, 267E, 268D, 268E, 327D, 327E, 328F, 328W, 328Y, and 332E. Exemplary substitutions include 235Y, 236D, 239D, 266M, 267E, 268D, 268E, 328F, 328W, and 328Y. Other Fc variants for enhancing binding to FcγRllb include 235Y/267E, 236D/267E, 239D/268D, 239D/267E, 267E/268D, 267E/268E, and 267E/328F.

The affinities and binding properties of an Fc region for its ligand may be determined by a variety of in vitro assay methods (biochemical or immunological based assays) known in the art including but not limited to, equilibrium methods (e.g., ELISA, or radioimmunoassay), or kinetics (e.g., BIACORE analysis), and other methods such as indirect binding assays, competitive inhibition assays, fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental immunology, 4th Ed., Lippincott-Raven, Philadelphia (1999), which focuses on antibody-immunogen interactions.

In certain embodiments, the antibody is modified to increase its biological half-life. Various approaches are possible. For example, this may be done by increasing the binding affinity of the Fc region for FcRn. For example, one or more of following residues can be mutated: 252, 254, 256, 433, 435, 436, as described in U.S. Pat. No. 6,277,375. Specific exemplary substitutions include one or more of the following: T252L, T254S, and/or T256F. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. Other exemplary variants that increase binding to FcRn and/or improve pharmacokinetic properties include substitutions at positions 259, 308, 428, and 434, including for example 259I, 308F, 428L, 428M, 434S, 434H, 434F, 434Y, and 434M. Other variants that increase Fc binding to FcRn include: 250E, 250Q, 428L, 428F, 250Q/428L (Hinton et al., 2004, J. Biol. Chem. 279(8): 6213-6216, Hinton et al. 2006 Journal of Immunology 176:346-356), 256A, 272A, 286A, 305A, 307A, 307Q, 311A, 312A, 376A, 378Q, 380A, 382A, 434A (Shields et al, Journal of Biological Chemistry, 2001, 276 (9):6591-6604), 252F, 252T, 252Y, 252W, 254T, 256S, 256R, 256Q, 256E, 256D, 256T, 309P, 311S, 433R, 433S, 4331, 433P, 433Q, 434H, 434F, 434Y, 252Y/254T/256E, 433K/434F/436H, 308T/309P/311S (Dall Acqua et al. Journal of Immunology, 2002, 169:5171-5180, Dall'Acqua et al., 2006, Journal of Biological Chemistry 281:23514-23524). Other modifications for modulating FcRn binding are described in Yeung et al., 2010, J Immunol, 182:7663-7671. In certain embodiments, hybrid IgG isotypes with particular biological characteristics may be used. For example, an IgG1/IgG3 hybrid variant may be constructed by substituting IgG 1 positions in the CH2 and/or CH3 region with the amino acids from IgG3 at positions where the two isotypes differ. Thus a hybrid variant IgG antibody may be constructed that comprises one or more substitutions, e.g., 274Q, 276K, 300F, 339T, 356E, 358M, 384S, 392N, 397M, 4221, 435R, and 436F. In other embodiments described herein, an IgG1/IgG2 hybrid variant may be constructed by substituting IgG2 positions in the CH2 and/or CH3 region with amino acids from IgG1 at positions where the two isotypes differ. Thus a hybrid variant IgG antibody may be constructed chat comprises one or more substitutions, e.g., one or more of the following amino acid substitutions: 233E, 234L, 235L, 236G (referring to an insertion of a glycine at position 236), and 321 h.

Moreover, the binding sites on human IgG1 for FcγR1, FcγRII, FcγRIII and FcRn have been mapped and variants with improved binding have been described (see Shields, R. L. et al. (2001) J. Biol. Chem. 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A, which has been shown to exhibit enhanced FcγRIIIa binding and ADCC activity (Shields et al., 2001). Other IgG1 variants with strongly enhanced binding to FcγRIIIa have been identified, including variants with S239D/I332E and S239D/I332E/A330L mutations which showed the greatest increase in affinity for FcγRIIIa, a decrease in FcγRIIb binding, and strong cytotoxic activity in cynomolgus monkeys (Lazar et al., 2006). Introduction of the triple mutations into antibodies such as alemtuzumab (CD52– specific), trastuzumab (HER2/neu-specific), rituximab (CD20– specific), and cetuximab (EGFR– specific) translated into greatly enhanced ADCC activity in vitro, and the S239D/I332E variant showed an enhanced capacity to deplete B cells in monkeys (Lazar et al., 2006). In addition, IgG1 mutants containing L235V, F243L, R292P, Y300L and P396L mutations which exhibited enhanced binding to FcγRIIIa and concomitantly enhanced ADCC activity in transgenic mice expressing human FcγRIIIa in models of B cell malignancies and breast cancer have been identified (Stavenhagen et al., 2007; Nordstrom et al., 2011). Other Fc mutants that may be used include: S298A/E333A/L334A, S239D/1332E, S239D/1332E/A330L, L235V/F243L/R292P/Y300L/P396L, and M428L/N434S.

In certain embodiments, an Fc is chosen that has reduced binding to FcγRs. An exemplary Fc, e.g., IgG1 Fc, with reduced FcγR binding comprises the following three amino acid substitutions: L234A, L235E and G237A.

In certain embodiments, an Fc is chosen that has reduced complement fixation. An exemplary Fc, e.g., IgG1 Fc, with reduced complement fixation has the following two amino acid substitutions: A330S and P331S.

In certain embodiments, an Fc is chosen that has essentially no effector function, i.e., it has reduced binding to FcγRs and reduced complement fixation. An exemplary Fc, e.g., IgG1 Fc, that is effectorless comprises the following five mutations: L234A, L235E, G237A, A330S and P331S.

When using an IgG4 constant domain, it is usually preferable to include the substitution S228P, which mimics the hinge sequence in IgG1 and thereby stabilizes IgG4 molecules.

Antibody Derivatives

An antibody provided herein may be further modified to contain additional nonproteinaceous moieties that are known in the art and readily available. The moieties suitable for derivatization of the antibody include but are not limited to water soluble polymers.

Non-limiting examples of water soluble polymers include, but are not limited to, PEG, copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Another modification of the antibodies described herein is pegylation. An antibody can be pegylated to, for example, increase the biological (e.g., serum) half-life of the antibody. To pegylate an antibody, the antibody, or fragment thereof, typically is reacted with PEG, such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (CI-CIO) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies described herein. See for example, EP 0 154 316 by Nishimura et al. and EP0401384 by Ishikawa et al.

The present invention also encompasses a human monoclonal antibody described herein conjugated to a therapeutic agent, a polymer, a detectable label or enzyme. In one embodiment, the therapeutic agent is a cytotoxic agent. In one embodiment, the polymer is PEG.

Methods of Productions

Antibodies may be produced using recombinant methods and compositions, e.g., as described in U.S. Pat. No. 4,816,567. In one embodiment, isolated nucleic acid encoding an antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g., a Chinese Hamster Ovary (CHO) cell or lymphoid cell (e.g., Y0, NS0, Sp20 cell). In one embodiment, a method of making an antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include CHO cells, including DHFR⁻ CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

Compositions and Formulations

The antibodies of this invention represent an excellent way for the development of antiviral therapies either alone or in antibody cocktails with additional anti-influenza virus antibodies for the treatment of human influenza infections in humans.

In another aspect, the present invention provides a pharmaceutical composition comprising the antibodies of the present invention described herein formulated together with a pharmaceutically acceptable carrier. The composition may optionally contain one or more additional pharmaceutically active ingredients, such as another antibody or a therapeutic agent. The pharmaceutical compositions of the invention also can be administered in a combination therapy with, for example, another immune-stimulatory agent, an antiviral agent, or a vaccine, etc. In certain embodiments, a composition comprises an antibody of this invention at a concentration of at least 1 mg/ml, 5 mg/ml, 10 mg/ml, 50 mg/ml, 100 mg/ml, 150 mg/ml, 200 mg/ml, 1-300 mg/ml, or 100-300 mg/ml.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., Remington: The Science and Practice of Pharmacy, 20th Ed. (Lippincott Williams & Wilkins 2003), the disclosure of which is incorporated herein by reference.

Preferably, a pharmaceutical composition is suitable for intravenous, intramuscular, subcutaneous, parenteral, spinal or epidermal administration (e.g., by injection or infusion). Depending on the route of administration, the active compound can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the present invention described herein can be administered via a non-parenteral route, such as a topical, epidermal or mucosal route of administration, e.g., intranasally, orally, vaginally, rectally, sublingually or topically.

The pharmaceutical composition of the invention can be in the form of pharmaceutically acceptable salts. A "pharmaceutically acceptable salt" refers to a salt that retains the desired biological activity of the parent compound and does not impart any undesired toxicological effects. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The pharmaceutical composition of the present invention can be in the form of sterile aqueous solutions or dispersions. It can also be formulated in a microemulsion, liposome, or other ordered structure suitable to high drug concentration.

An antibody of the present invention described herein can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably, until the patient shows partial or complete amelioration of symptoms of disease. Thereafter, the patient can be administered a prophylactic regime.

The amount of active ingredient that can be combined with a carrier material to produce a single dosage form will vary depending upon the subject being treated and the particular mode of administration and will generally be that amount of the composition, which produces a therapeutic effect. Generally, out of one hundred percent, this amount will range from about 0.01% to about 99% of active ingredient, preferably from about 0.1% to about 70%, most preferably from about 1% to about 30% of active ingredient in combination with a pharmaceutically acceptable carrier.

Dosage regimens can be adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. Alternatively, antibody can be administered as a sustained release formulation, in which case less frequent administration is required. For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 µg/ml and in some methods about 25-300 µg/ml. A "therapeutically effective dosage" of an antibody of the invention preferably results in a decrease in severity of disease symptoms, an increase in frequency and duration of disease symptom-free periods, or a prevention of impairment or disability due to the disease affliction. For example, for the treatment of influenza infection in a subject, a "therapeutically effective dosage" preferably inhibits influenza virus replication or uptake by host cells by at least about 20%, more preferably by at least about 40%, even more preferably by at least about 60%, and still more preferably by at least about 80% relative to untreated subjects. A therapeutically effective amount of a therapeutic compound can neutralize influenza virus, or otherwise ameliorate symptoms in a subject, which is typically a human or can be another mammal. The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparati (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the human monoclonal antibodies of the invention described herein can be formulated to ensure proper distribution in vivo. For example, to ensure that the therapeutic compounds of the invention cross the blood-brain barrier, they can be formulated in liposomes, which may additionally comprise targeting moieties to enhance selective transport to specific cells or organs. See, e.g., U.S. Pat. Nos. 4,522,811; 5,374,548; 5,416,016; and 5,399,331; V. V. Ranade (1989) Clin. Pharmacol. 29:685; Umezawa et al, (1988) Biochem. Biophys. Res. Commun. 153:1038; Bloeman et al. (1995) FEBS Lett. 357:140; M. Owais et al. (1995) Antimicrob. Agents Chemother. 39:180; Briscoe et al. (1995) Am. Physiol. 1233:134; Schreier et al. (1994). Biol. Chem. 269:9090; Keinanen and Laukkanen (1994) FEBS Lett. 346:123; and Killion and Fidler (1994) Immunomethods 4:273.

Uses and Methods

The current anti-viral treatments (e.g., oseltamivir/Tamiflu, amantadine/rimantadine) for influenza are sub-optimal with increasing incidence of resistance and a limited therapeutic window (must start <48 hours after symptom onset) (Beigel J, et al. 2008. Antiviral Res 78:91-102; Garcia-Sastre A. 2006. Emerg Infect Dis 12:44-47; and Marathe B M, et al. 2016. Sci Rep 6:26742). Monoclonal antibodies continue to be a growing class of drugs in part due to their high degree of specificity, limited off-target effects, and superb safety profile. The antibodies, compositions and formulations described herein can be used to neutralize influenza virus and thereby treating influenza infections.

Accordingly, in one aspect, the antibodies described herein can be used to neutralize influenza virus. The neutralizing of the influenza virus can be done via (i) inhibiting influenza virus binding to a target cell; (ii) inhibiting influenza virus uptake by a target cell; (iii) inhibiting influenza virus replication; and (iv) inhibiting influenza virus particles release from infected cells. One skilled in the art possesses the ability to perform any assay to assess neutralization of influenza virus. Notably, the neutralizing properties of antibodies may be assessed by a variety of tests, which all may assess the consequences of (i) inhibition of influenza virus binding to a target cell; (ii) inhibition of influenza virus uptake by a target cell; (iii) inhibition of influenza virus replication; and (iv) inhibition of influenza virus particles release from infected cells. In other words, implementing different tests may lead to the observation of the same consequence, i.e., the loss of infectivity of the influenza virus. Thus, in one embodiment, the present invention provides a method of neutralizing influenza virus in a subject comprising administering to the subject a therapeutically effect amount of the antibody of the present invention described herein.

Another aspect of the present invention provides a method of treating an influenza-related disease. Such method includes therapeutic (following influenza infection) and prophylactic (prior to influenza exposure, infection or pathology). For example, therapeutic and prophylactic methods of treating an individual for an influenza infection include treatment of an individual having or at risk of having an influenza infection or pathology, treating an individual with an influenza infection, and methods of protecting an individual from an influenza infection, to decrease or reduce the probability of an influenza infection in an individual, to decrease or reduce susceptibility of an individual to an influenza infection, or to inhibit or prevent an influenza infection in an individual, and to decrease, reduce, inhibit or suppress transmission of an influenza from an infected individual to an uninfected individual. Such methods include administering an antibody of the present invention or a composition comprising the antibody disclosed herein to therapeutically or prophylactically treat (vaccinate or immunize) an individual having or at risk of having an influenza infection or pathology. Accordingly, methods can treat the influenza infection or pathology, or provide the individual with protection from infection (e.g., prophylactic protection).

In one embodiment, a method of treating an influenza-related disease comprises administering to an individual in need thereof an antibody or therapeutic composition disclosed herein in an amount sufficient to reduce one or more physiological conditions or symptom associated with an influenza infection or pathology, thereby treating the influenza-related disease.

In one embodiment, an antibody or therapeutic composition disclosed herein is used to treat an influenza-related disease. Use of an antibody or therapeutic composition disclosed herein treats an influenza-related disease by reducing one or more physiological conditions or symptom associated with an influenza infection or pathology. In aspects of this embodiment, administration of an antibody or therapeutic composition disclosed herein is in an amount sufficient to reduce one or more physiological conditions or symptom associated with an influenza infection or pathology, thereby treating the influenza-based disease. In other aspects of this embodiment, administration of an antibody or therapeutic composition disclosed herein is in an amount sufficient to increase, induce, enhance, augment, promote or stimulate influenza clearance or removal; or decrease, reduce, inhibit, suppress, prevent, control, or limit transmission of influenza to another individual.

One or more physiological conditions or symptom associated with an influenza infection or pathology will respond to a method of treatment disclosed herein. The symptoms of influenza infection or pathology vary, depending on the phase of infection.

In another aspect of the present invention, the antibody described herein can be used in various detection methods, for use in, e.g., monitoring the progression of an influenza infection; monitoring patient response to treatment for such an infection, etc. The present disclosure provides methods of detecting a neuraminidase polypeptide in a biological sample obtained from an individual. The methods generally involve: a) contacting the biological sample with a subject anti-neuraminidase antibody; and b) detecting binding, if any, of the antibody to an epitope present in the sample. In some instances, the antibody comprises a detectable label. The level of neuraminidase polypeptide detected in the biological sample can provide an indication of the stage, degree, or severity of an influenza infection. The level of the neuraminidase polypeptide detected in the biological sample can provide an indication of the individual's response to treatment for an influenza infection.

The antibodies described herein can be used together with one or more of other anti-influenza virus antibodies to neutralize influenza virus and thereby treating influenza infections.

Definitions

The term "antibody" as referred to herein includes whole antibodies and any antigen-binding fragment or single chains thereof. Whole antibodies are glycoproteins comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $C_H1$, $C_H2$ and $C_H3$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The heavy chain variable region CDRs and FRs are HFR1, HCDR1, HFR2, HCDR2, HFR3, HCDR3, HFR4. The light chain variable region CDRs and FRs are LFR1, LCDR1, LFR2, LCDR2, LFR3, LCDR3, LFR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antigen-binding fragment or portion" of an antibody (or simply "antibody fragment or portion"), as used herein, refers to one or more fragments of an antibody that retain the ability to specifically bind to an antigen (e.g., a neuraminidase of influenza A or B virus). It has been shown that the antigen-binding function of an antibody can be performed by fragments of a full-length antibody. Examples of binding fragments encompassed within the term "antigen-binding fragment or portion" of an antibody include (i) a Fab fragment, a monovalent fragment consisting of the $V_L$, $V_H$, $C_L$ and $C_H1$ domains; (ii) a F(ab')2 fragment, a bivalent fragment comprising two Fab fragments linked by a disulfide bridge at the hinge region; (iii) a Fab' fragment, which is essentially an Fab with part of the hinge region (see, FUNDAMENTAL IMMUNOLOGY (Paul ed., $3^{rd}$ ed. 1993)); (iv) a Fd fragment consisting of the $V_H$ and $C_H1$ domains; (v) a Fv fragment consisting of the $V_L$ and VH domains of a single arm of an antibody, (vi) a dAb fragment (Ward et al., (1989) Nature 341:544-546), which consists of a VH domain; (vii) an isolated CDR; and (viii) a nanobody, a heavy chain variable region containing a single variable domain and two constant domains. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv or scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding fragment or portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds to a neuraminidase of influenza A or B virus is substantially free of antibodies that specifically bind antigens other than the neuraminidase). An isolated antibody can be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody" is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity, which have variable regions in which both the framework and CDR regions are derived from human germline immunoglobulin sequences. In one embodiment, the human monoclonal antibodies can be produced by a hybridoma that includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "isotype" refers to the antibody class (e.g., IgM or IgG1) that is encoded by the heavy chain constant region genes. The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody. The term "humanized antibody" is intended to refer to antibodies in which CDR sequences derived from the germline of another mammalian species, such as a mouse, have been grafted onto human framework sequences. Additional framework region modifications can be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody. The term can also refer to an antibody in which its variable region sequence or CDR(s) is derived from one source (e.g., an IgA1 antibody) and the constant region sequence or Fc is derived from a different source (e.g., a different antibody, such as an IgG, IgA2, IgD, IgE or IgM antibody).

As used herein, the term "affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (KD). Affinity can be measured by common methods known in the art, including those described herein.

As used herein, an antibody that "specifically binds to a neuraminidase of influenza virus" refers to an antibody that binds to a neuraminidase of influenza virus but does not substantially bind to non-influenza virus neuraminidase. Preferably, the antibody binds to the neuraminidase with "high affinity", namely with a KD of $1\times10^{-7}$ M or less, more preferably $5\times10^{-8}$ M or less, more preferably $3\times10^{-8}$ M or less, more preferably $1\times10^{-8}$ M or less, more preferably $5\times10^{-9}$ M or less or even more preferably $1\times10^{-9}$ M or less. The term "does not substantially bind" to a protein or cells, as used herein, means does not bind or does not bind with a high affinity to the protein or cells, i.e., binds to the protein or cells with a KD of $1\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more.

The term "Kassoc" or "Ka", as used herein, is intended to refer to the association rate of a particular antibody-antigen interaction, whereas the term "Kdis" or "Kd," as used herein, is intended to refer to the dissociation rate of a particular antibody-antigen interaction. The term "KD," as used herein, is intended to refer to the dissociation constant, which is obtained from the ratio of Kd to Ka (i.e., Kd/Ka) and is expressed as a molar concentration (M). KD values for antibodies can be determined using methods well established in the art. A preferred method for determining the KD of an antibody is by using surface plasmon resonance, preferably using a biosensor system such as a Biacore® system.

The term "epitope" as used herein refers to an antigenic determinant that interacts with a specific antigen-binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immune-precipitation assays, wherein overlapping or contiguous peptides from a neuraminidase protein are tested for reactivity with a given antibody. Methods of determining spatial conformation of epitopes include techniques in the art and those described herein, for example, x-ray crystallography and 2-dimensional nuclear magnetic resonance (see, e.g., Epitope Mapping Protocols in Methods in Molecular Biology, Vol. 66, G. E. Morris, Ed. (1996)).

The term "epitope mapping" refers to the process of identification of the molecular determinants for antibody-antigen recognition.

The term "binds to an epitope" or "recognizes an epitope" with reference to an antibody or antibody fragment refers to continuous or discontinuous segments of amino acids within an antigen. Those of skill in the art understand that the terms do not necessarily mean that the antibody or antibody fragment is in direct contact with every amino acid within an epitope sequence.

The term "binds to the same epitope" with reference to two or more antibodies means that the antibodies bind to the same, overlapping or encompassing continuous or discontinuous segments of amino acids. Those of skill in the art understand that the phrase "binds to the same epitope" does not necessarily mean that the antibodies bind to or contact exactly the same amino acids. The precise amino acids that the antibodies contact can differ. For example, a first antibody can bind to a segment of amino acids that is completely encompassed by the segment of amino acids bound by a second antibody. In another example, a first antibody binds one or more segments of amino acids that significantly overlap the one or more segments bound by the second antibody. For the purposes herein, such antibodies are considered to "bind to the same epitope."

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, may be determined using known competition experiments. In certain embodiments, an antibody competes with, and inhibits binding of another antibody to a target by at least 10%, 20%, 30%, 40%, 50%, 60%, 70%, 80%, 90% or 100%. The level of inhibition or competition may be different depending on which antibody is the "blocking antibody" (i.e., the cold antibody that is incubated first with the target). Competition assays can be conducted as described, for example, in Ed Harlow and David Lane, Cold Spring Harb Protoc; 2006; doi: 10.1101/pdb.prot4277 or in Chapter 11 of "Using Antibodies" by Ed Harlow and David Lane, Cold Spring Harbor Laboratory Press, Cold Spring Harbor, NY, USA 1999. Competing antibodies bind to the same epitope, an overlapping epitope or to adjacent epitopes (e.g., as evidenced by steric hindrance). Other competitive binding assays include: solid phase direct or indirect radioimmunoassay (RIA), solid phase direct or indirect enzyme immunoassay (EIA), sandwich competition assay (see Stahli et al., Methods in Enzymology 9:242 (1983)); solid phase direct biotin-avidin EIA (see Kirkland et al., J. Immunol. 137:3614 (1986)); solid phase direct labeled assay, solid phase direct labeled sandwich assay (see Harlow and Lane, Antibodies: A Laboratory Manual, Cold Spring Harbor Press (1988)); solid phase direct label RIA using 1-125 label (see Morel et al., Mol. Immunol. 25(1):7 (1988)); solid phase direct biotin-avidin EIA (Cheung et al., Virology 176:546 (1990)); and direct labeled RIA. (Moldenhauer et al., Scand. J. Immunol. 32:77 (1990)).

As used herein, the term "immune response" refers to a biological response within a vertebrate against foreign agents, which response protects the organism against these agents and diseases caused by them. An immune response is mediated by the action of a cell of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune reaction includes, e.g., activation or inhibition of a T cell, e.g., an effector T cell or a Th cell, such as a CD4+ or CD8+ T cell, or the inhibition of a Treg cell.

The term "detectable label" as used herein refers to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, streptavidin or haptens), intercalating dyes and the like. The term "fluorescer" refers to a substance or a portion thereof that is capable of exhibiting fluorescence in the detectable range.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "therapeutically effective amount" of a compound of the present invention refers to an amount of the compound of the present invention that will elicit the biological or medical response of a subject, or ameliorate symptoms, slow or delay disease progression, or prevent a disease, etc. In one embodiment, the term refers to the amount that inhibits or reduces microbial colonization or infection. In one embodiment, the term refers to the amount that inhibits or reduces infection, or prevent or destroying the formation of bacterial biofilms. When applied to an individual active ingredient, administered alone, the term refers to that ingredient alone. When applied to a combination, the term refers to combined amounts of the active ingredients that result in the therapeutic effect, whether administered in combination, serially or simultaneously.

As used herein, the term "pharmaceutically acceptable carrier or excipient" refers to a carrier medium or an excipient which does not interfere with the effectiveness of the biological activity of the active ingredient(s) of the composition and which is not excessively toxic to the host at the concentrations at which it is administered. In the context of the present invention, a pharmaceutically acceptable carrier or excipient is preferably suitable for topical formulation. The term includes, but is not limited to, a solvent, a stabilizer, a solubilizer, a tonicity enhancing agent, a structure-forming agent, a suspending agent, a dispersing agent, a chelating agent, an emulsifying agent, an antifoaming agent, an ointment base, an emollient, a skin protecting agent, a gel-forming agent, a thickening agent, a pH adjusting agent, a preservative, a penetration enhancer, a complexing agent, a lubricant, a demulcent, a viscosity enhancer, a bioadhesive polymer, or a combination thereof. The use of such agents for the formulation of pharmaceutically active substances is well known in the art (see, for example, "Remington's Pharmaceutical Sciences", E. W. Martin, 18th Ed., 1990, Mack Publishing Co.: Easton, PA, which is incorporated herein by reference in its entirety).

As used herein, the term "treating" or "treatment" of any disease or disorder refers in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The term "about" refers to within 10%, preferably within 5%, and more preferably within 1% of a given value or range. Alternatively, the term "about" refers to within an acceptable standard error of the mean, when considered by one of ordinary skill in the art.

EXAMPLES

Example 1

This example describes material and methods used in Examples 2-7 bellow.

Subjects. Peripheral blood was obtained from 17 healthy adult subjects prior to, 7 days, and 1 month after receiving the 2014 to 2015 seasonal QUADRIVALENT IIV [SANOFI PASTEUR FLUZONE; A/California/07/2009 X-179A (H1N1) pdm09, A/Texas/50/2012 X-223A (H3N2), B/Massachusetts/2/2012, and B/Brisbane/60/2008 viruses] as the standard of care at the University of Rochester Medical Center. A 50-ml volume of bone marrow aspirate was obtained from the posterior iliac crest. The subjects provided signed written informed consent. All procedures and methods were approved by the Research Subjects Review Board at the University of Rochester Medical Center, and all experiments were performed in accordance with relevant guidelines and regulations. Peripheral blood mononuclear cells (PBMC) and plasma were isolated using cell preparation tubes (CPT) (BECTON, DICKINSON, Franklin Lakes, NJ, USA).

Cells and viruses. MDCK; ATCC CCL-34) and human embryonic kidney (HEK293T; ATCC CRL-11268) cells were grown in DULBECCO's modified Eagle's medium (DMEM; MEDIATECH, INC.) that had been enriched with 5% fetal bovine serum (FBS) and 1% PSG (penicillin, 100 units/ml; streptomycin, 100 µg/ml; L-glutamine, 2 mM) at 37° C. with 5% $CO_2$.

Recombinant influenza virus A/California/4_NYICE_E3/ 2009 (pH1N1), B/Yamagata/16/1988, and B/Brisbane/60/ 2008 WT or mCherry-expressing viruses have been previously described. A reassortant IBV containing the six internal genes (PB2, PB1, PA, NP, M, and NS-mCherry) from B/Brisbane/60/2008 virus and the HA and NA from B/Yamagata/16/1988 (reB/Yamagata/16/1988 mCherry) virus was generated using plasmid-based reverse genetics techniques. Two recombinant B/Brisbane/60/2008 virus strains containing amino acid substitution E117A or H273Y (E119A or H274Y [N2 numbering]) in the NA were generated using plasmid-based reverse genetics techniques. IBV B/Malaysia/2506/2004 (NR-9723), B/Ohio/01/2005 (NR-41801), B/Nevada/03/2011 (NR-44023), B/Sydney/507/ 2006 (NR-36526), B/Texas/06/2011 (NR-44024), and B/Lee/1940 (NR-3178) were obtained from BEI RESOURCES, and the IBV B/Wisconsin/01/2010 (FR-806) was obtained from INTERNATIONAL REAGENT RESOURCES (IRR). Viral titrations were performed and stocks were produced in MDCK cells at 33° C. For infections, virus stocks were diluted in phosphate-buffered saline (PBS)-0.3% bovine albumin (BA)-1% penicillin-streptomycin (PS) (PBS/BA/PS). After viral infections were performed, cells were maintained in post infection (p.i.) medium containing DMEM, 0.3% BA, 1% PSG, and 1 µg/ml tosylsulfonyl phenylalanyl chloromethyl ketone (TPCK)-treated trypsin (SIGMA). Viral titers were determined by an immuno-focus assay using MDCK cells and an anti-HA goat polyclonal antibody (BEI RESOURCES; NR-3165), as previously described, and the titers are presented as levels of FFU per milliliter.

Generation and screening of human monoclonal antibodies. Fresh PBMC collected 7 days after immunization were stained for flow cytometry as previously described. Plasmablasts (CD19+ IgD− CD38+CD27++) were subjected to direct single-cell sorting performed with a FACSARIA cell sorter (BD BIOSCIENCES) and were placed into 96-well PCR plates (BIO-RAD, Hercules, CA) containing 4 µl of a mixture of 0.5×PBS, 10 mM dithiothreitol (DTT) (INVITROGEN), and 8 U RIBOLOCK (THERMO FISHER) RNase inhibitor per well. Plates were sealed with ALUMASEAL 96 sealing foil (EXCEL SCIENTIFIC, Inc.) and immediately frozen at −80° C. until use for reverse transcription-PCR (RT-PCR). cDNA was synthesized, and nested PCR was performed for IgH, Igλ, and Igκ V gene transcripts, followed by linear Ig cassette generation as previously described. Human embryonic kidney cells (HEK293T; ATCC CRL-11268) were seeded into 96-well flat-bottom plates at 27,000 cells/well in DMEM-10% HYCLONE FETALCLONE II (GE HEALTHCARE LIFE SCIENCES, Logan, UT)-1× antibiotic/antimycotic (GIBCO, LIFE TECHNOLOGIES, Grand Island, NY). Cultures achieved 70% to 80% confluence within 48 h of incubation at 37° C. with 5% $CO_2$. The medium was changed to 100 µl per well of DMEM-2.5% HYCLONE FETALCLONE II-1× antibiotic/antimycotic (2.5% FCII). Purified linear cassettes were transfected using JETPRIME transfection reagent (POLYPLUS, New York, NY). Approximately 48 h later, an additional 150 µl of 2.5% FCII was added to each well and plates incubated for another 3 days before the medium containing the secreted IgG was harvested. Harvested medium was screened on ELISA plates (NUNC MAXISORP; THERMO FISHER SCIENTIFIC, Rochester, NY) coated with 0.5 µg/ml recombinant IBV NA protein (B/Florida/04/2009; BEI RESOURCES, Manassas, VA) and detected with horseradish peroxidase (HRP)-conjugated anti-human IgG (JACKSON IMMUNORESEARCH, West Grove, PA). Plates were read at 450 nm using the optical density (OD) readings at 650 nm to subtract background levels. Wells were designated "positive" with OD values greater than 3-fold the OD of the negative control (PBS).

To generate a permanent plasmid containing positive hMAbs, purified PCR products were sequenced at GENEWIZ INC. (South Plainfield, NJ) and analyzed by IGBLAST and IMGT/V-QUEST to identify the germline V(D)J gene segments with the highest identity and to determine sequence properties. Expression vector cloning and transfection of human HEK293T cells were performed as previously described. IgG was purified from culture supernatant using MAGNA protein G or A beads (PROMEGA, Madison, WI). 1069 D6 is a human IgG1 MAb and was used as an isotype control.

Binding characterization (ELISA and avidity). ELISA plates (NUNC MAXISORP; THERMO FISHER SCIENTIFIC, Grand Island, NY) were coated with recombinant NA or HA proteins (BEI RESOURCES, Manassas, VA) at 1 μg/ml or with respiratory syncytial virus (RSV) fusion (F) protein at 0.5 μg/ml, hMAbs or plasma was diluted in PBS, and binding was detected with HRP-conjugated anti-human IgG (JACKSON IMMUNO-RESEARCH, West Grove, PA). Plasma was tested in 5-fold dilutions (1:100 to 1:62,500), and area under the curve (AUC) values were determined. In selected ELISAs, increasing concentrations of urea were added to the ELISA plate and the plates incubated for 15 min at room temperature prior to detection with anti-IgG-HRP to evaluate avidity.

Virus neutralization and fluorescence-based microneutralization assays. Virus neutralization assays were performed with WT and mCherry-expressing viruses as previously described. Briefly, confluent monolayers of MDCK cells ($5 \times 10^4$ cells/well, 96-well plate format, triplicates) were infected with 200 FFUs of indicated viruses. After 1 h viral adsorption, cells were maintained at 33° C. in p.i. medium supplemented with 1 μg/ml TPCK-treated trypsin and 2-fold serial dilutions of the indicated hMAbs (starting concentration, 10 μg/ml). For the fluorescence-based microneutralization assays, at 48 to 72 h p.i., cell monolayers were washed with PBS prior to red fluorescence quantification using a fluorescence plate reader (DTX-880; BECTON DICKENSON). Fluorescence values of mCherry virus-infected cells in the absence of hMAb were used to calculate 100% viral infection. Cells in the absence of viral infection were used to calculate the fluorescence background. WT virus neutralization was determined by crystal violet staining at 96 to 120 h p.i. Triplicate wells were used to calculate the mean and SD of neutralization, and $IC_{50}$ values were determined with a sigmoidal dose response curve (GRAPHPAD PRISM, v7.0).

Enzyme-linked lectin assay (ELLA). The ability of IBV NA hMAbs to inhibit the activity of the viral NA was measured using a standard ELLA as previously described. Briefly, 2-fold serial dilutions of the hMAbs (starting concentration, 1 μg/ml) were preincubated with B/Brisbane/60/2008 or B/Yamagata/16/1988 WT viruses at a predetermined concentration of virus for 2 h at room temperature in DULBECCO's PBS (DPBS) (GIBCO) supplemented with 1% bovine serum albumin (BSA) (diluent buffer). Virus-hMAb dilutions were added to 96-well plates coated with 50 μg/ml of fetuin (SIGMA) and incubated for 18 h at 37° C. Then, plates were extensively washed with PBS containing 0.05% Tween 20 and incubated with HRP-coupled peanut lectin agglutinin (SIGMA) in diluent buffer for 2 h at room temperature. After washing of the plates with PBS-TWEEN, the reactions were developed with 3',5,5-tetramethylbenzidine (TMB) substrate (BIOLEGEND) for 15 to 20 min at room temperature, quenched with 2 N $H_2SO_4$, and read at 450 nm (VMAX kinetic microplate reader; MOLECULAR DEVICES). The IC50 was determined with a sigmoidal dose response curve (GRAPHPAD PRISM, v7.0).

Immunofluorescence assay. Confluent monolayers of MDCK cells ($2 \times 10^5$ cells/well, 24-well plate format) were mock infected or infected (multiplicity of infection [MOI] of 0.1) with the indicated WT viruses. At 17 h p.i., cells were fixed with 4% paraformaldehyde (PFA) and permeabilized with 0.5% TRITON X-100-PBS for 15 min at room temperature. Cells were then incubated for 1 h at 37° C. with 1 μg/ml of IBV NA-specific hMAbs or with IAV HA hMAb KPF1 as a control. Then, cells were incubated with fluorescein isothiocyanate (FITC)-conjugated secondary anti-human Ab (DAKO) for 1 h at 37° C. Images were captured using a fluorescence microscope (OLYMPUS IX81) and camera (QIMAGING, RETIGA 2000R) with a 10× objective.

Antibody-secreting cell enzyme-linked immunosorbent spot (ELISpot) assays. The frequency of influenza antigen-specific antibody-secreting cells (ASCs) was measured by ELISpot assay as previously described. Briefly, ELISpot assay plates were coated overnight with either recombinant NA (5 μg/ml B/Florida/04/2009 or B/Hong Kong/330/2001 virus; BEI RESOURCES, Manassas, VA, USA) or FLUZONE IIV vaccine (6 μg/ml, SANOFI PASTEUR INC., Swiftwater, PA, USA) and incubated at 37° C. for about 40 h with 500,000 or 100,000 PBMC. Bound antibodies were detected with alkaline phosphatase-conjugated anti-human IgG (JACKSON IMMUNORESEARCH) (1 μg/ml). Spots in each well were counted using a CTL immunospot reader (CELLULAR TECHNOLOGIES LTD., Shaker Heights, OH, USA).

Prophylactic and therapeutic protective activities of NA-specific hMAbs in mice. Female C57BL/6 mice (5 to 7 weeks of age) were purchased from the National Cancer Institute (NCI) and maintained in the animal care facility at the University of Rochester under specific-pathogen-free conditions. All animal protocols were approved by the University of Rochester Committee of Animal Resources and complied with the recommendations in the Guide for the Care and Use of Laboratory Animals of the National Research Council. For viral infections, mice were anesthetized i.p. with 2,2,2-tribromoethanol (AVERTIN; 240 mg/kg of body weight) and were then inoculated intranasally with $10^6$ FFU of influenza B/Brisbane/60/2008 WT virus in a final volume of 30 μl. To determine the prophylactic efficacy of the NA hMAbs, at 6 h before infection, mice (n=6) were subjected to i.p. administration of 20 mg/kg of the hMAbs, an irrelevant isotype control 1069 D6 hMAb, or PBS. For the study of therapeutic efficacy, at 24 h p.i., groups of mice (n=6) were given i.p injections of 20 mg/kg of the indicated NA hMAbs, the isotype control IgG, or PBS. Viral replication was determined in the lungs of the infected mice at days 2 and 4 p.i. To determine the levels of replication, three mice from each group were euthanized by administration of a lethal dose of avertin and exsanguination and lungs were surgically extracted and homogenized. Virus titers (FFU per milliliter) were determined by immunofocus assay as indicated above. Geometric mean titers and data representation were performed using GRAPHPAD PRISM (v7.0).

Deep-sequencing immunoglobulin repertoire analysis. PBMC were isolated from whole blood collected into CPT as described above. In addition to the samples collected 7 days after immunization, PBMC were also isolated from blood samples collected more than 2 months prior to vaccination, 7 weeks after vaccination, and more than 15 months after vaccination. For the final blood sample, approximately 50 million PBMC were used to enrich for B cells by using biotinylated anti-CD3, anti-CD4, and anti-CD14 antibodies along with antibiotin microbeads (MILTENYI BIOTEC, Auburn, CA) in a negative selection. Bone marrow aspirate was obtained at more than 12 months following the influenza vaccination, and mononuclear cells were isolated by floating the cells over FICOLL-PAQUE PLUS medium (GE HEALTHCARE BIOSCIENCES, Pittsburgh, PA). Approximately 40 million cells were then used with CD138 microbeads (MILTENYI BIOTEC) to isolate the CD138-positive fraction according to the manufacturer's protocol. The entire positive fraction was lysed in RLT buffer (QIAGEN, Hilden, Germany; catalog no. 79216) and stored at −80° C. until RNA isolation could be performed. RNA was isolated from all samples using an RNEASY MINIKIT (QIAGEN), treated with DNase I (TURBO DNA-FREE kit; INVITROGEN, Vilnius, Lithuania), and used to synthesize cDNA with a QSCRIPT cDNA synthesis kit (QUANTABIO, Beverly, MA). The resulting cDNA was used in subsequent PCR using PLATINUM TAQ high-fidelity polymerase (INVITROGEN, Carlsbad, CA) as previously described. Targeted PCR was performed to try to detect lineage members of the cloned monoclonal antibodies by using forward primers specific for VH3-15 (TAARAGGTGTCCAGTGT, SEQ ID NO: 74) and VH3-23 (AGTTTGGGCTGAGCTGGCTT, SEQ ID NO: 75). Gel-extracted PCR products were submitted to the University of Rochester Genomics Research Center, where QUBIT fluorometric quantitation (THERMO FISHER) and BIOANALYZER (AGILENT TECHNOLOGIES, Santa Clara, CA) sizing, quantitation, and quality control were performed prior to normalization to 2 nM and flow cell hybridization and cluster generation for a MISEQ system (ILLUMINA, Inc., San Diego, CA). Paired-end reads (300 by 325 bp) were made. Sequence analysis and assembly of lineage trees were performed using an in-house custom analysis pipeline as previously described. All sequences were aligned using IMGT.ORG/HIGHVQUEST. Lineage trees were generated by identifying the lineage (the cluster of sequences with identical VH, JH, and HCDR3 lengths and >85% HCDR3 similarity) containing the corresponding MAb sequence. Sequences within a lineage with single occurrences of particular VDJ nucleotide sequences (singletons) were removed, with the exception of singletons obtained from CD138bone marrow samples. The resulting sequences were analyzed using PHYLIP'S PROTPARS tool (version 3.695), turning on settings 1, 4, and 5. The output file was then parsed using in-house custom scripts, collapsing any duplicate inferred sequences into an individual node, and was visualized using CYTOSCAPE.

Statistical analysis. Significance was determined using GRAPHPAD PRISIM, v7.0. Paired t tests were applied for evaluation of the results of the serum binding antibody assessment, and the Mann-Whitney test was used for evaluation of the results of the ELISPOT assessment. One-way analysis of variance (ANOVA) was used to determine the statistical significance of the in vivo viral titers.

Example 2

Figure 1C:
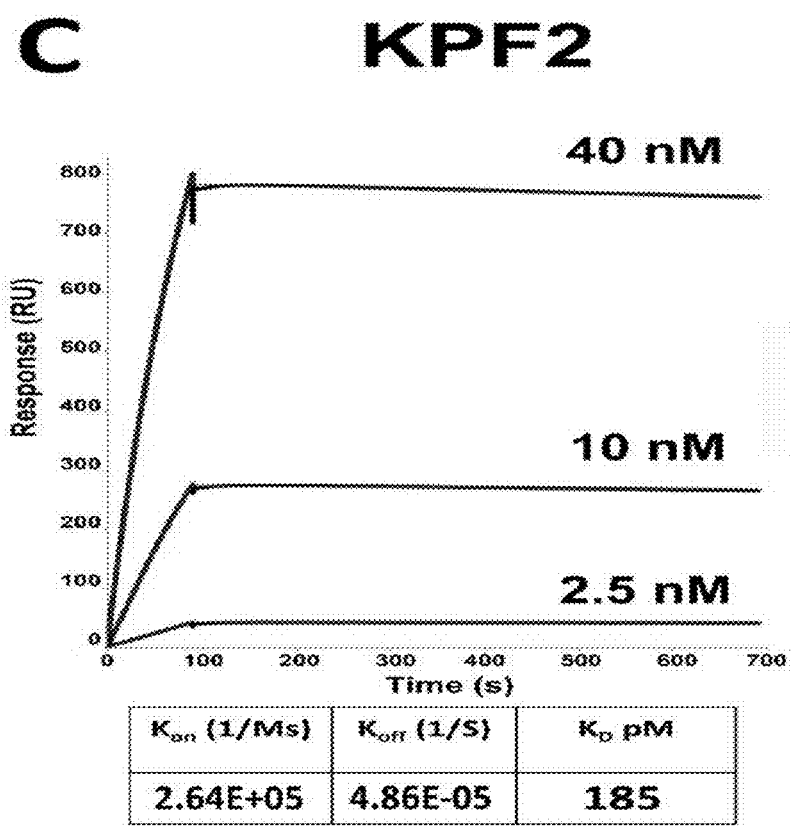
FIG. 1C is a diagram showing that the affinity of KPF2 for NA B/Hong Kong/330/2001 was determined by surface plasmon resonance with KPF2 bound to the chip and NA flowed over at different concentrations.

Influenza N2 and NB specific human monoclonal antibodies were isolated from peripheral blood plasmablasts. Briefly, plasmablasts (CD19+IgD-CD38+CD27++) were single cell sorted from peripheral blood 1 week following immunization and subjected to RT-PCR to amplify and clone the immunoglobulin heavy and light chain variable regions to obtain recombinant hmAbs. HmAbs were screened by ELISA for NA reactivity. Three N2-specific (FIG. 1A) and six NB specific hmAbs (FIG. 1B) were tested for binding to multiple NA proteins by ELISA. As shown in FIG. 1C, the affinity of KPF2 was for NA B/Hong Kong/330/2001 was determined by surface plasmon resonance with KPF2 bound to the chip and NA flowed over at different concentrations.

The immunoglobulin gene usage and mutation from germline was determined by sequencing and IGBLAST analysis. The results are shown in the table below.

TABLE 1

Molecular characteristics of NA-specific hmAbs.

| | | | Heavy chain | | Light chain | |
|---|---|---|---|---|---|---|
| target | hmAb | Native Isotype | gene usage | mutation (% nt/% aa) | gene usage | mutation (% nt/% aa) |
| N2 | 1092 A9 | IgG1 | VH3-23 DH2-21 JH6 | 6/13 | Vκ1-33 Jκ4 | 3/6 |
| | 1092 B6 | IgG1 | VH1-24 DH3-10 JH6 | 7/13 | Vκ3-20 Jκ1 | 6/7 |
| | 1092 G4 | IgG1_ | VH1-24 DH3-10 JH6 | 5/8 | Vκ3-20 Jκ1 | 2/3 |
| NB | KPF2 (1092D4) | IgG1 | VH3-23 DH3-3 JH4 | 8/9 | Vλ6-57 Jλ3 | 4/7 |
| | 1086 C12 | IgG1 | VH3-30 DH3-22 JH5 | 9/15 | Vλ1-47 Jλ2 | 4/6 |
| | 1086 F8 | IgG1 | VH3-30 DH3-22 JH4 | 7/10 | Vλ1-47 Jλ2 | 7/10 |
| | 1092 E10 | IgG1 | VH3-15 DH3-16 JH6 | 6/9 | Vλ3-1 Jλ1 | 5/11 |
| | 1122 C6 | IgA1 | VH4-59 DH1-26 JH5 | 5/10 | Vλ3-25 Jλ2 | 5/9 |
| | 1122 C7 | IgG1 | VH3-23 DH3-3 JH4 | 8/8 | Vλ6-57 Jλ3 | 4/6 |

Figure 2A:
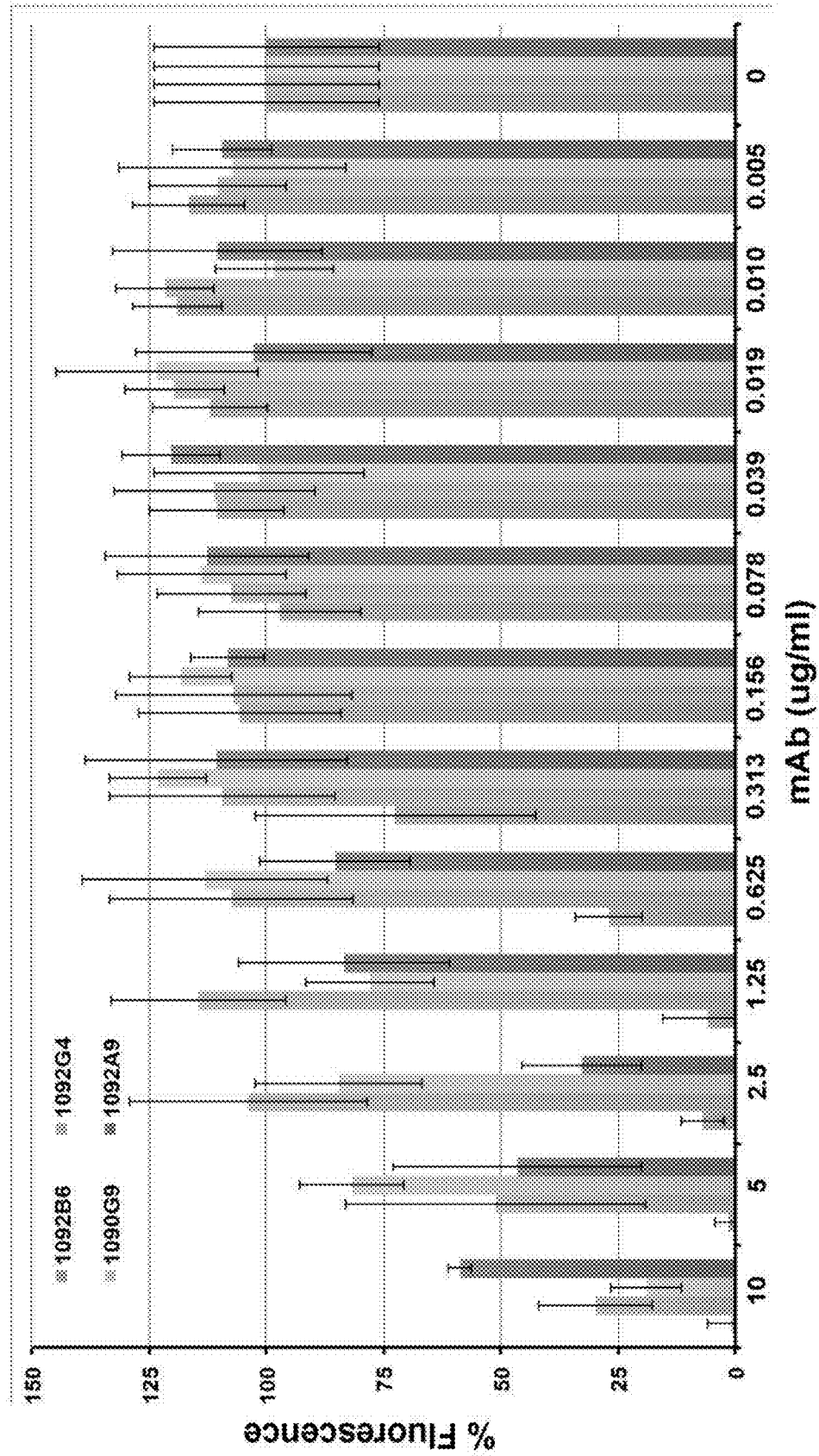
Figure 2B:
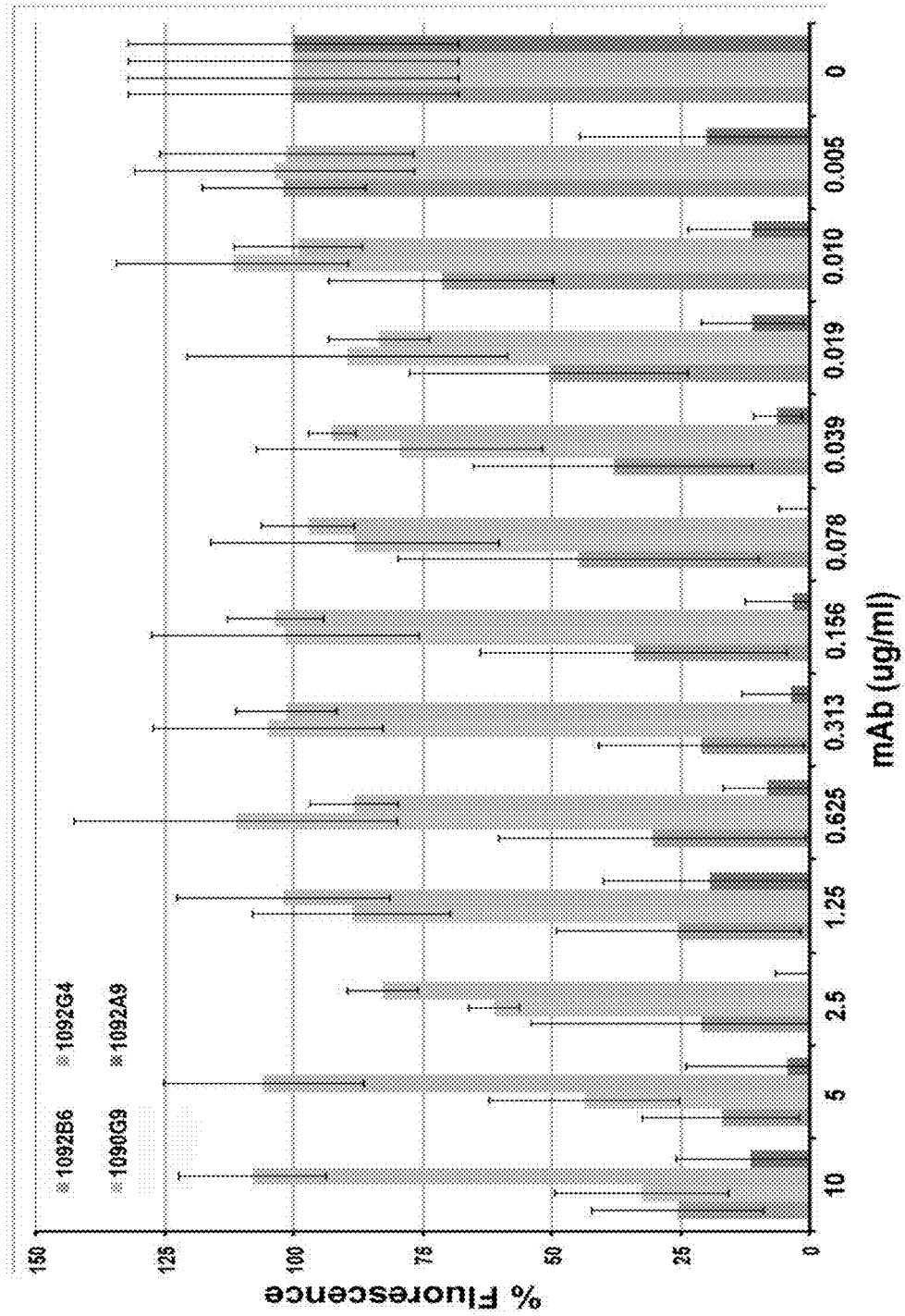

The in vitro neutralizing activity of the antibodies were then examined. MDCK cells were infected with 100 PFU of indicated virus and then 1 h later hmAb dilutions were added and cultures incubated in quadruplicates for 48-60 h. Viral infection was quantitated by fluorescence detection or crystal violet staining (B/Yamagata/16/88). As shown in FIGS. 2A-2C. N2 and NB hmAbs exhibited in vitro neutralizing activity.

Figure 3:
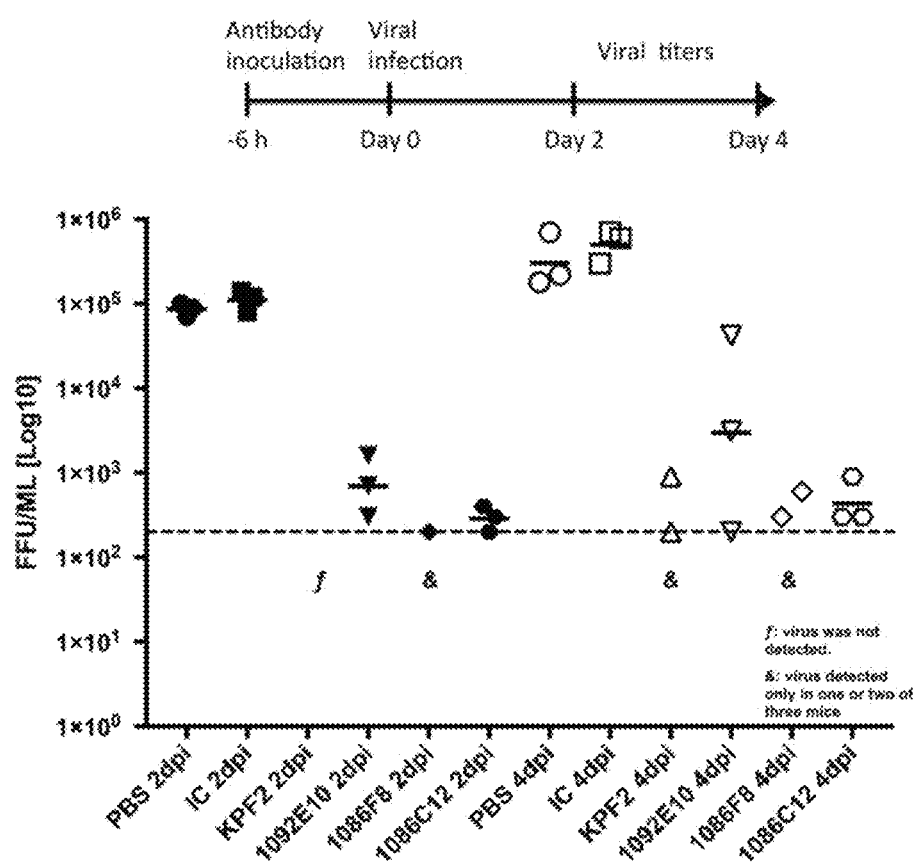
FIG. 3 is a diagram showing that hmAbs specific to NB confer protection from B/Brisbane/60/2008 infection. C57BL/6 mice (n=6/group) received 20 mg/kg of isotype control (IC) or NB-specific hmAb intraperitoneally and then 6 h later were challenged with 106 PFU of B/Brisbane/60/2008 virus. Lung virus was measured at 2 d and 4 d post-infection.

Assays were carried out to examine whether hmAbs specific to NB confer protection from viral infection. C57BL/6 mice (n=6/group) received 20 mg/kg of isotype control or NB-specific hmAb intraperitoneally and then 6 h later were challenged with 106 PFU of B/Brisbane/60/2008 virus. Lung virus was measured at 2 d and 4 d post-infection. As shown in FIG. 3, hmAbs specific to NB confred protection from B/Brisbane/60/2008 infection.

Figure 4:
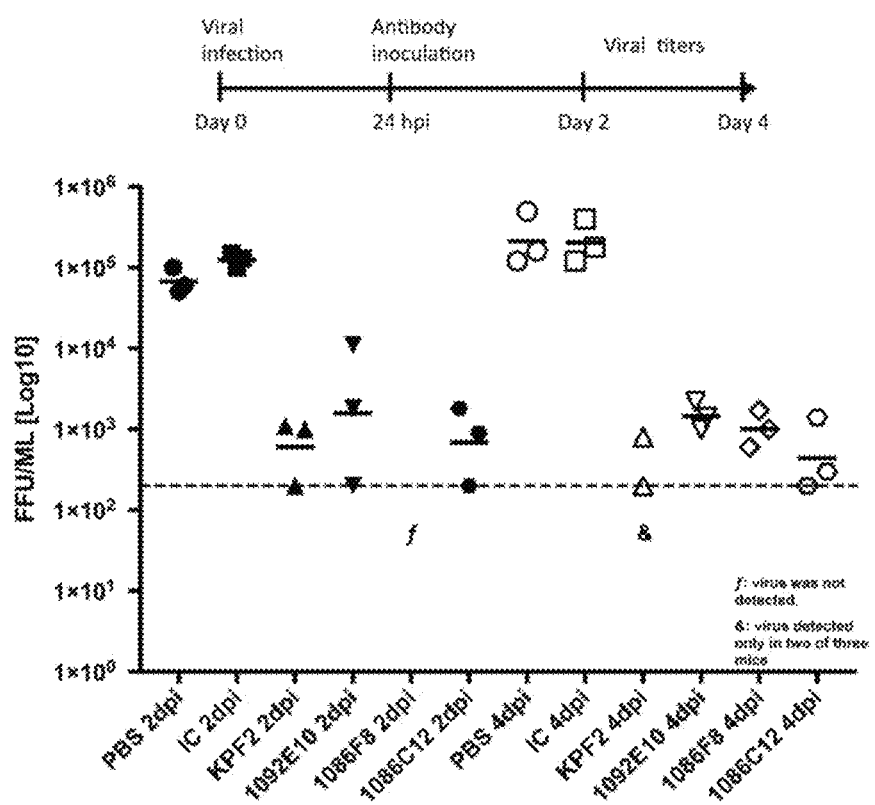
FIG. 4 is a diagram showing that hmAbs specific to NB have therapeutic activity against B/Brisbane/60/2008 infection. C57BL/6 mice (n=6/group) were challenged with $10^6$ PFU of B/Brisbane/60/2008 virus and then 24 h post-infection received 20 mg/kg of IC or NB-specific hmAb intraperitoneally. Lung virus was measured at 2 d and 4 d post-infection.

C57BL/6 mice (n=6/group) were challenged with $10^6$ PFU of B/Brisbane/60/2008 virus and then 24 h post-infection received 20 mg/kg of IC or NB-specific hmAb intraperitoneally. Lung virus was measured at 2 d and 4 d post-infection. As shown in FIG. 4, hmAbs specific to NB have therapeutic activity against B/Brisbane/60/2008 infection.

Example 3

Figures 5A, 5B:
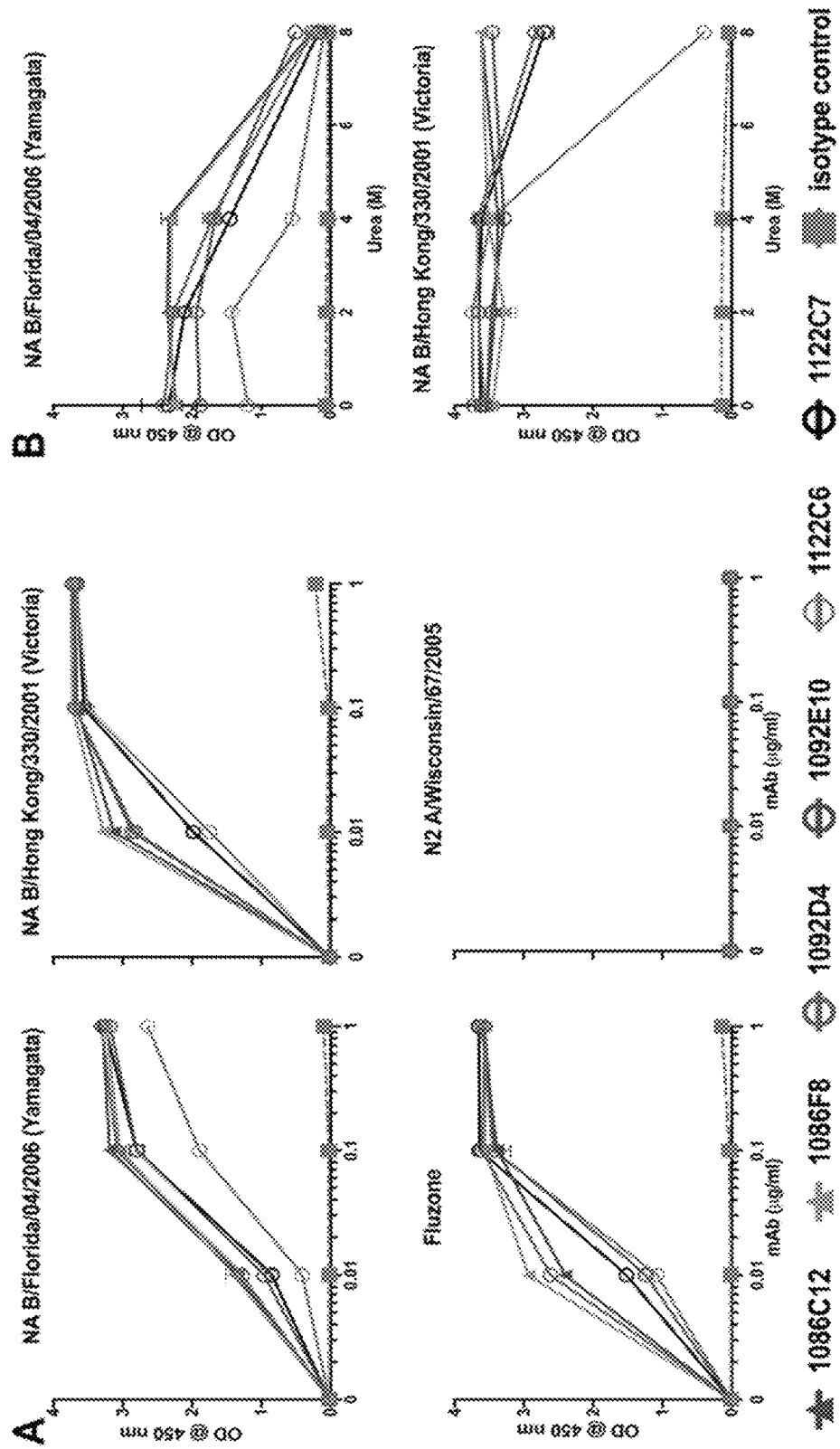
FIGS. 5A, 5B, and 5C are diagrams and photographs showing that Influenza B virus (IBV) NA-specific hMAbs recognize Victoria and Yamagata lineages. IBV NA-specific hMAbs were generated from plasmablasts following inactivated influenza vaccines (IIV) immunization.

As mentioned above, to define the characteristics and functional potential of IIV-induced IBV NA-specific antibodies, D7 plasmablasts were sorted as single cells from two subjects (105 and 134) who demonstrated increased levels IBV NA-specific plasma IgG, and their expressed immunoglobulin heavy chain and light chain variable regions were cloned to generate recombinant fully hMAbs. Subsequently, six IBV NA-specific hMAbs were isolated that exhibited strong binding to recombinant IBV NA protein from the Victoria (B/Hong Kong/330/2001) and Yamagata (B/Florida/04/2006) virus lineages, in addition to the 2016/2017 IIV (FLUZONE) (FIG. 5A).

No reactivity to IAV N2 was detected, indicating the highly specific binding of these IBV NA hMAbs. The stability of the binding of the hMAbs to NA was accessed by treatment with increasing urea concentrations. All hMAbs maintained greater than 75% of their binding activity against IBV NA B/Hong Kong/330/2001 in 8 M urea treatment, with the exception of 1122C6, which had reduced binding stability. These hMAbs similarly maintained their binding activity against NA B/Florida/04/2006 in 4 M urea, but the level was substantially diminished in 8 M urea (FIG. 5B). Binding affinity was further tested using the 1092D4 hMAb and surface plasmon resonance. 1092D4 bound both B/Hong Kong/330/2001 and B/Florida/04/2006 NA proteins with very high affinity; specifically, the equilibrium dissociation constants of binding were 100 and 185 pM, respectively.

Figure 5C:
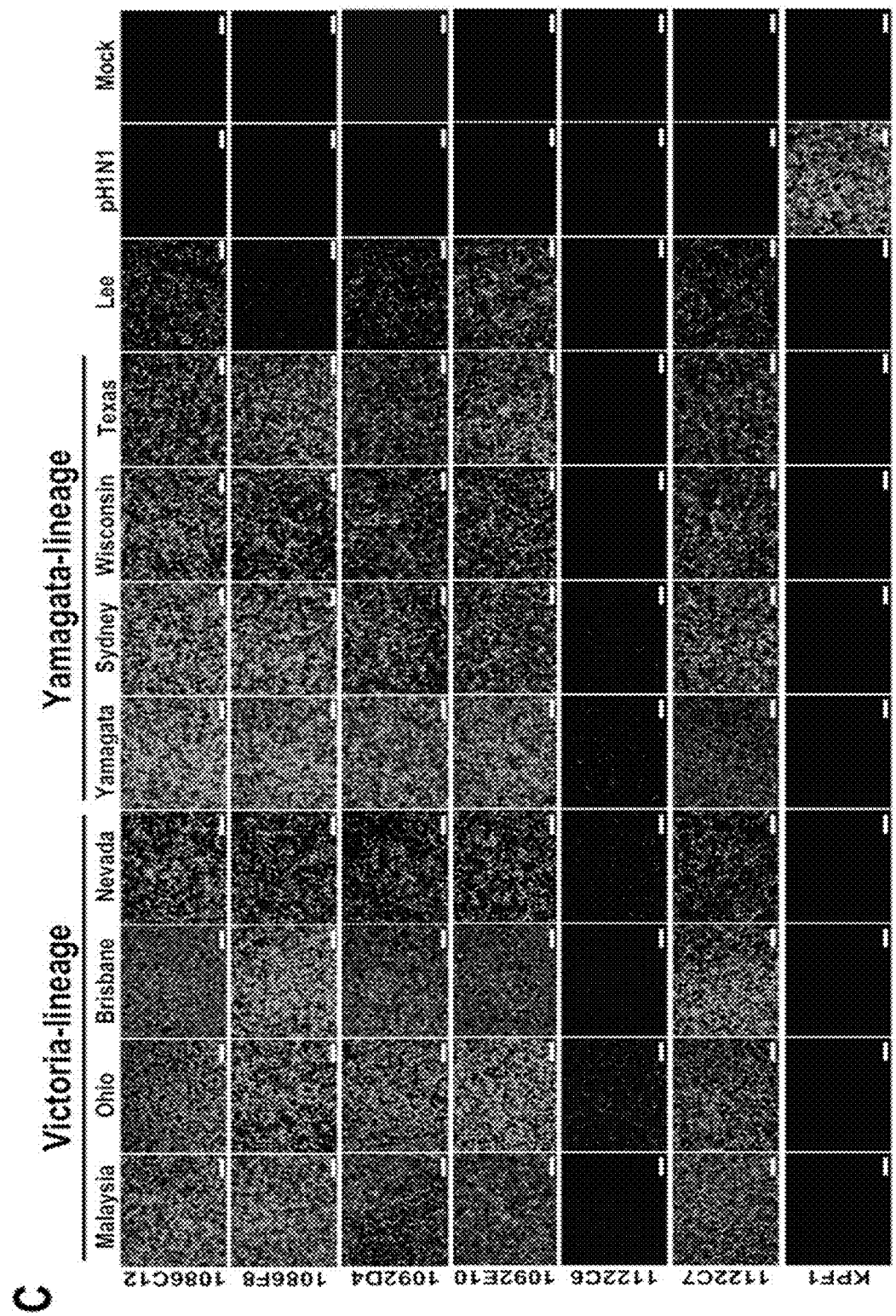

To define the ability of the IBV-specific hMAbs to recognize native NA, MDCK cells were infected with IAV (A/California/04/09 H1N1) or IBV viruses and hMAb binding evaluated by IFA. All IBV hMAbs, with the exception of 1122C6, recognized all Victoria and Yamagata lineage IBV tested. Additionally, 1092D4, 1092E10, 1086C12, and 1122C7 also recognized the common ancestor B/Lee/40 virus strain (FIG. 5C). HMAb 1122C6 exhibited the most limited breadth, with substantial binding only to IBV B/Ohio/01/2005 (Victoria lineage)-infected cells consistent with its stronger binding to NA B/Hong Kong/330/2001 by ELISA (FIG. 5A). These results indicate that IIV-induced plasmablasts include high-affinity broadly reactive IBV NA-specific hMAbs.

Example 4

The two hMAbs cloned from subject 134 (1086C12 and 1086F8) may be clonally related as they share the same variable heavy (VH3-30) and lambda light (Vλ1-47) chain gene usage and CDR3 lengths and show 77% HCDR3 and 86% LCDR3 homology. The VH chain of hMAb 1086C12 showed higher levels of mutation from the germline VH3-30 than 1086F8, but the Vλ of 1086F8 showed greater mutation from the Vλ1-47 germline than 1086C12. Likewise, hMAbs 1092D4 and 1122C7 are clonally related, sharing the same variable heavy (VH3-23) and light (Vλ6-57) chain gene usage, with similar degrees of mutation from the germline. These two hMAbs also have identical examples of λCDR3 and of HCDR3, differing only in the terminal residue (1092D4=D, 1122C7=E). The NA-specific 1092E10 hMAb has the distinction of having the longest (22 amino acids) HCDR3 among the hMAbs. All of the IBV NA-specific hMAbs exhibited modest mutation from germline (VH, 8% to 15% amino acids (aa); VL, 6% to 11% aa), suggesting that affinity maturation had occurred. Examining the native heavy chain constant region sequence that was expressed by the plasmablast from which the hMAbs were cloned, with the exception of 1122C6, which was IgA1, all were IgG1.

Example 5

Figures 6A, 6B:
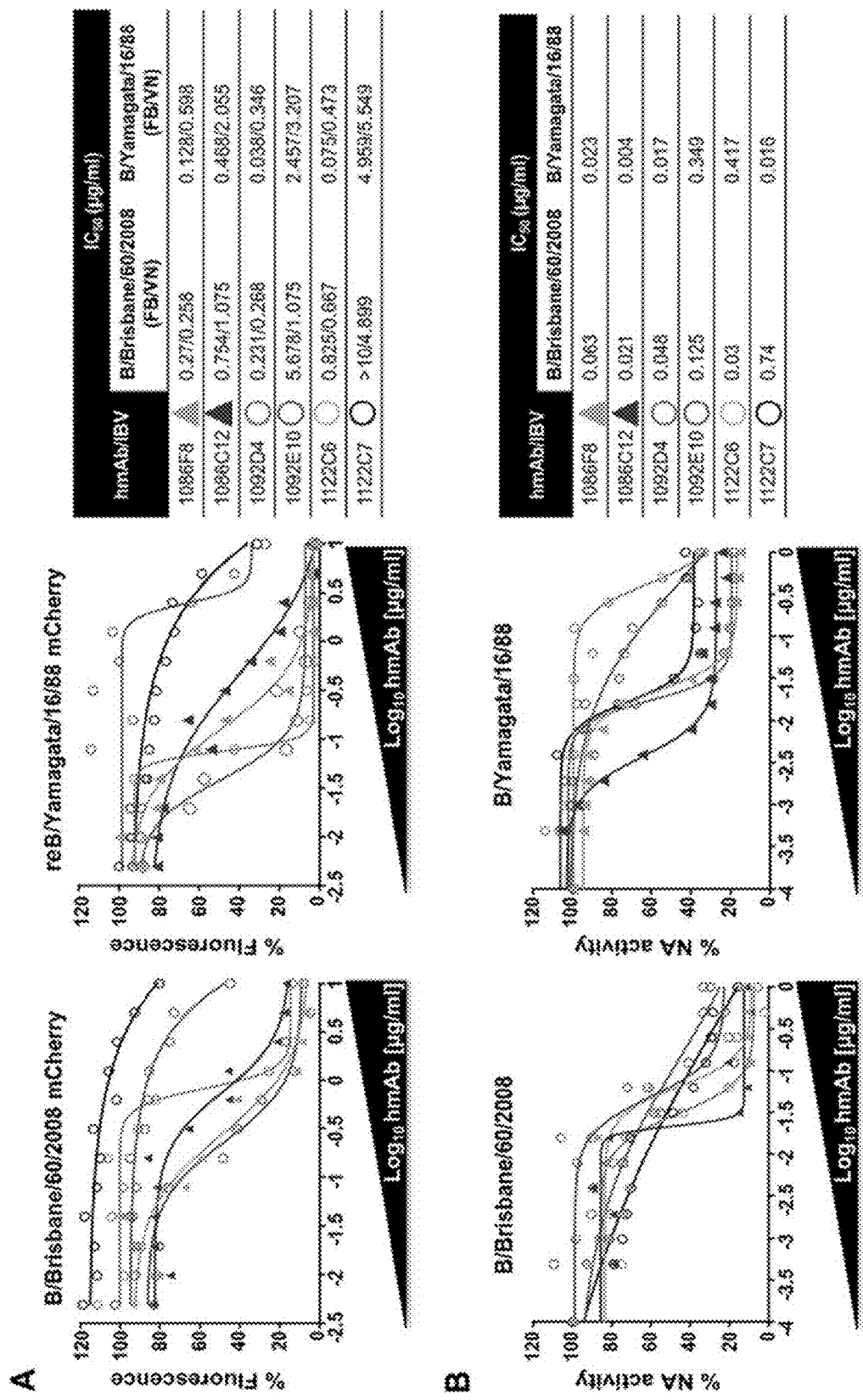
FIGS. 6A, 6B, and 6C are diagrams and photographs showing ability of IBV NA-specific hMAbs to inhibit viral infection and NA activity.

In this example, inventors next evaluated the ability of the 6 identified IBV NA hMAbs to inhibit viral infection by using a fluorescence-based microneutralization assay. For that, MDCK cells were infected with mCherry-expressing influenza B/Brisbane/60/2008 virus, which is a representative member of Victoria lineage, and then incubated with 2-fold serial dilutions of the IBV NA hMAbs (starting concentration, 10 µg/ml) followed by quantification of the levels of inhibition (FIG. 6A). Notably, hMAbs 1086C12, 1086F8, 1092D4, 1092E10, and 1122C6 displayed dose-dependent inhibition activity against virus infection, although with different levels of efficacy, with 1092E10 being the least potent hMAb. However, hMAb 1122C7 did not show significant inhibition at the concentrations tested in the assay (FIG. 6A).

In order to determine if the inhibitory activity of the IBV NA hMAbs was specific for IBV of the Victoria lineage or if they also have the ability to inhibit IBV of the Yamagata lineage, a plasmid-based reverse genetic system was used to generate a recombinant mCherry-expressing virus containing the six internal genes (PB2, PB1, PA, NP, M and NS-mCherry) from B/Brisbane/60/2008 virus and the HA and NA from influenza B/Yamagata/16/1988 virus, a representative member of the Yamagata lineage. Then, the ability of the six IBV NA hMAbs to inhibit infection was evaluated using the fluorescence-based microneutralization assay described above. Notably, as observed previously with mCherry-expressing B/Brisbane/60/2008 virus, the most effective neutralizing hMAbs were 1086C12, 1086F8, 1092D4, and 1122C6. Moreover, hMAbs 1092E10 and 1122C7 showed inhibition only at the higher concentrations (FIG. 6A). The ($IC_{50}$ values, determined using a classical sigmoidal dose response curve, showed that the levels of inhibition of the two mCherry-expressing virus strains were similar (FIG. 6A).

Then a conventional VN assay was used to further assess inhibition of influenza B/Brisbane/60/2008 and B/Yamagata/16/1988 WT viruses by the 6 IBV NA-specific hMAbs. The results showed comparable levels of inhibition for the WT and mCherry viruses (FIG. 6A). Moreover, the VN data correlated with the data previously observed in the fluorescence approach as shown by the percentage of inhibition calculated using sigmoidal dose responses (FIG. 6A). hMAb 1092D4 exhibited the greatest potency across all infectivity assays (IC50'<0.5 µg/ml) followed by 1086C12 and 1122C6 (IC50'<1.0 µg/ml) and 1086F8 (IC50'<5.0 µg/ml), with 1092E10 and 1122C7 having the weakest activity.

The main function for viral NA is cleavage of the sialic acid residues on the cell surface, permitting the release of mature virions that then infect new cells. Therefore, to better understand the inhibitory mechanism for the IBV NA hMAbs, the sialic acid cleavage was evaluated by using ELLA with influenza B/Brisbane/60/2008 and B/Yamagata/16/1988 WT viruses as antigens (FIG. 6B). Interestingly, all the hMAbs efficiently inhibited the activity of the viral NA in both viral strains (FIG. 6B).

Figure 6C:
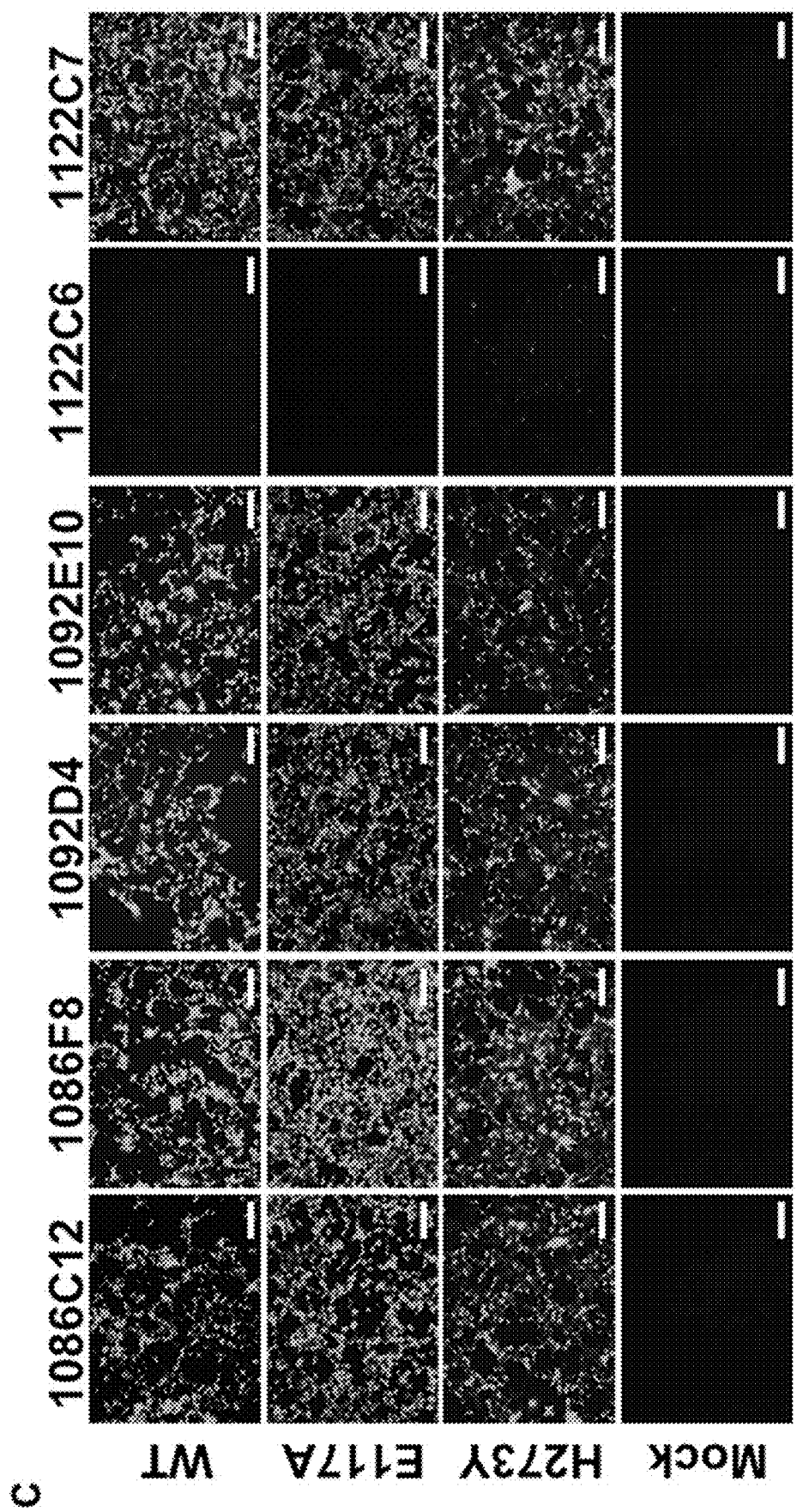

Moreover, assays were carried out to evaluate the ability of the IBV NA hMAbs to bind the NA from two recombinant B/Brisbane/60/2008 virus strains containing amino acid substitution E117A or H273Y (E119A or H274Y [N2 numbering]), which have been previously described to be resistant to oseltamivir. For that, MDCK cells infected with WT or mutant viruses were probed with the panel of hMAbs by immunofluorescence assay. All IBV hMAbs recognized the infected cells similarly, independently of the virus used (FIG. 6C). Taken together, these findings suggest that IBV NA hMAbs inhibit virus spread by inhibiting NA enzymatic activity and thus blocking the release of progeny virions from the infected cells, with 1092D4, 1086C12, 1086F8, and 1122C6 being more effective in vitro than 1092E10 and 1122C7.

Example 6

Given the broad and robust in vitro neutralization activity of the IBV NA-specific hMAbs, assays were carried out to investigate the in vivo protective breadth of the IBV NA hMAb panel, using a mouse model of infection (FIG. 9).

Figures 9A, 9B:
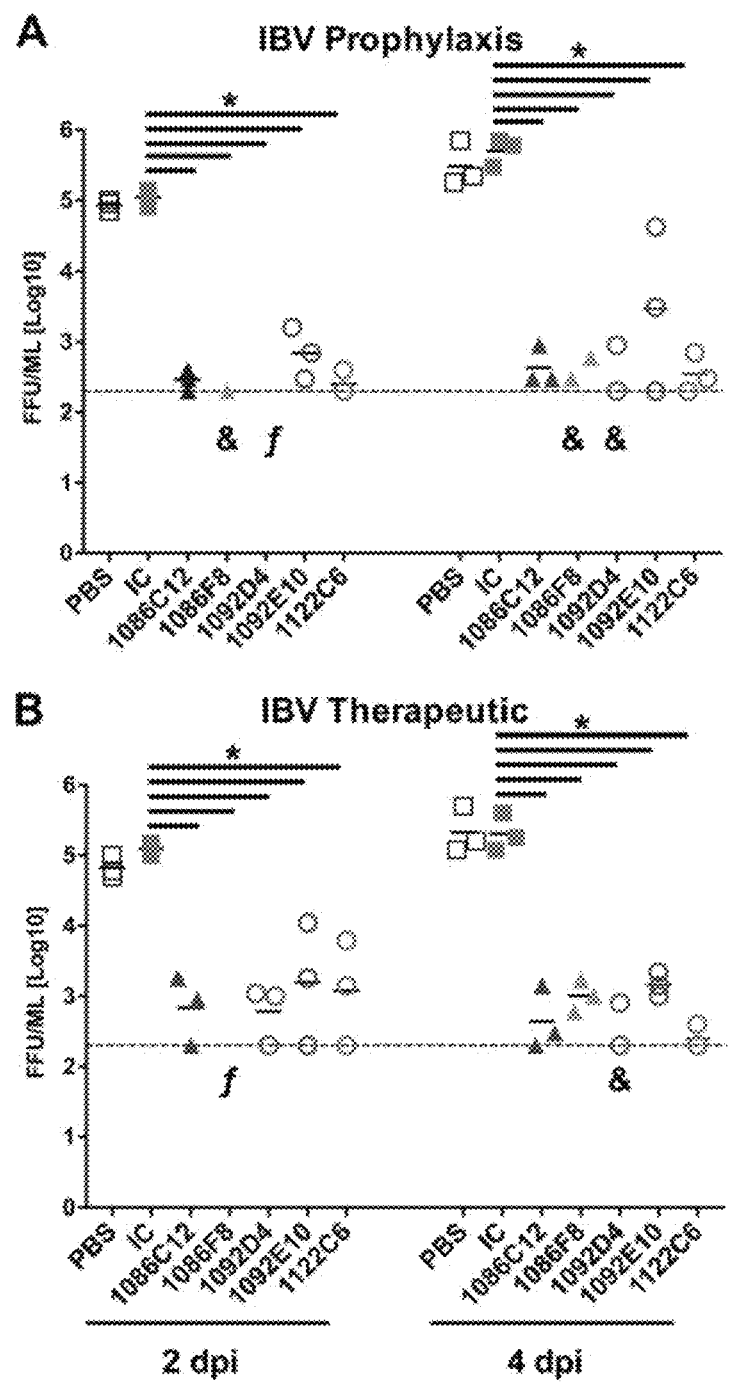
FIGS. 9A and 9B are diagrams showing in vivo prophylactic and therapeutic activity of the IBV hMAbs. (A) Prophylactic activity. Female C57BL/6 mice (n=3 per group/time point) were administered the indicated IBV NA hMAbs at 20 mg/kg i.p. or the irrelevant IC 1069 D6 hMAb at 20 mg/kg i.p. At 6 h after dosing, mice were inoculated i.n, with $1 \times 10^6$ FFU B/Brisbane/60/2008. (B) Therapeutic activity. Female C57BL/6 mice (n=3 per group) were inoculated i.n, with $1 \times 10^6$ FFU B/Brisbane/60/2008 and 24 h later were administered the indicated IBV NA hMAb or the irrelevant IC 1069 D6 hMAb at 20 mg/kg i.p. Viral replication (A and B) was determined by measuring viral titers in the lungs of the infected mice at 2 and 4 days post infection (dpi). Each symbol represents an individual mouse. The "&" symbol indicates that virus was detected in only one or two mice per group. "f" indicates that virus was not detected in any mouse

First, to evaluate the prophylactic efficacy of the IBV NA hMAbs, groups of mice received IBV NA hMAbs 1086F8, 1086C12, 1092D4, 1092E10, and 1122C6; an IgG isotype control hMAb; or PBS only. HMAbs were administered i.p. at 20 mg/kg of body weight, a dose that was selected based on previous studies evaluating other anti-NA MAbs and on the in vitro activity observed. The hMAbs were given 6 h before intranasal (i.n.) challenge with $10^6$ FFU of influenza B/Brisbane/60/2008 WT virus (FIG. 9A). hMAb 1122C7 was not included in these studies since the in vitro infectivity assays showed a low level of efficacy against B/Brisbane/60/2008 virus (FIG. 6A). Viral titers in the lungs of the infected mice were determined on days 2 (n=3) and 4 (n=3) p.i. and used as a measure of viral inhibition (FIG. 9A). Mice treated with the IgG isotype control hMAb or with PBS showed high and similar viral titers of about $10^5$ to $5 \times 10^5$ FFU/ml in the lungs at days 2 and 4 p.i. Notably, mice that received the IBV NA hMAbs showed significantly (P<0.05) lower viral titers or no detectable virus in the lungs of infected animals at those times (FIG. 9A). IBV NA hMAbs 1092D4 and 1086F8 were the most effective, with no virus detected in 1092D4-treated mice and virus detected in only one of three 1086F8-treated mice at day 2 p.i. At day 4 p.i., viral replication was lowest in the 1092D4-treated and 1086F8-treated mice, with the level being below the limit of detection in one mouse from each group. Both 1086C12 and 1122C6 suppressed viral replication to 200 to 900 FFU/ml, levels just above detection. The viral load in lungs of mice treated with 1092E10 was on average slightly higher than in animals treated with the other IBV NA hMAbs with higher variability. Those data correlated with the data from our in vitro inhibition assays (FIG. 6), where 1092E10 was the less potent hMAb, though still it was efficient with respect to inhibition of influenza B/Brisbane/60/2008 virus infection.

The therapeutic efficacy of the IBV NA hMAbs was also assessed (FIG. 9B). To that end, groups of mice infected with $10^6$ FFU of influenza B/Brisbane/60/2008 WT virus were treated with 20 mg/kg of IBV NA hMAbs at 24 h p.i. In addition, control groups of animals treated with the IgG isotype control hMAb or with PBS were included (FIG. 9B). To assess if the treatment with the IBV NA hMAbs could reduce lung viral loads, viral replication in lungs from infected mice was measured on days 2 (n=3) and 4 (n=3) p.i. Compared to the control treated groups, and correlating with the prophylactic analysis, treatment of mice with IBV NA hMAbs significantly (P<0.05) reduced the level of virus replication in the lungs of the infected mice (FIG. 9B).

Taken together, these data indicate that the identified MAbs have potent prophylactic and therapeutic activity against IBV infection in vivo and that they can significantly reduce virus dissemination in lungs.

Example 7

Long-lived bone marrow plasma cells are presumed to be the primary source of sustained circulating Abs. To determine if the IBV NA-specific hMAbs isolated from D7 plasmablasts persisted in long-lived bone marrow plasma cells, bone marrow was obtained from subject 105 1 year later, a time at which IBV NA-specific plasma IgG was still detectable. Bone marrow CD138+ plasma cells, total bone marrow B cells, and D7 total peripheral blood B cells were subjected to VH3-targeted deep sequencing of the immunoglobulin repertoire. Members of the 1092E10 clonal lineage were identified among CD138+ plasma cells and total bone marrow B cells, with many of the CD138+ plasma cells exhibiting additional somatic hypermutation beyond that seen with the 1092E10 hMAb. Similarly, members of the 1092D4/1122C7 clonal lineage were found within the CD138+ plasma cells, including those with VH sequences identical to those also found in D7 total peripheral blood B cells. These results indicate that IBV NA-specific B cell lineages with protective potential persist within the CD138+ long-lived bone marrow plasma cell repertoire following IIV immunization.

Each of the hMAbs tested bound recombinant and native IBV NA and potently ($IC_{50}$, <0.5 µg/ml) inhibited the NA enzymatic activity of IBV from both the Yamagata and Victoria lineages and, with the exception of 1122C7, also potently ($IC_{50}$, <5 µg/ml) inhibited the replication of IBV from both lineages. This substantial antiviral breadth spanned more than 2 decades of isolates for all the hMAbs and greater than 7 decades for the 1086C12, 1092D4, 1092E01, and 1122C7 hMAbs, which also recognized the ancestral B/Lee/1940 virus isolate, suggesting that sufficiently conserved epitopes are present across a wide range of IBV isolates. The hMAbs' inhibition of NA enzymatic activity and yet their ability to recognize IBV with mutations in NA that confer oseltamivir resistance suggest that the hMAbs' binding is not dependent on E117 or H273 but on other epitopes within the NA active site or within sufficient proximity to the active site to sterically hinder the access of substrate to the active site.

All of the IBV NA-specific hMAbs tested demonstrated prophylactic and therapeutic activity against IBV infection in mice, consistent with their in vitro antiviral and NA inhibitory properties. In particular, 1086F8 and 1092D4, which exhibited the greatest in vivo activity against B/Brisbane/60/2008 virus, including suppressing the virus to below detectable levels in several mice, were the most potent hMAbs in inhibiting B/Brisbane/60/2008 virus replication in vitro ($IC_{50}$, <0.5 µg/ml) but were not superior to the other hMAbs in their ELLA activity.

Example 8

Figure 7:
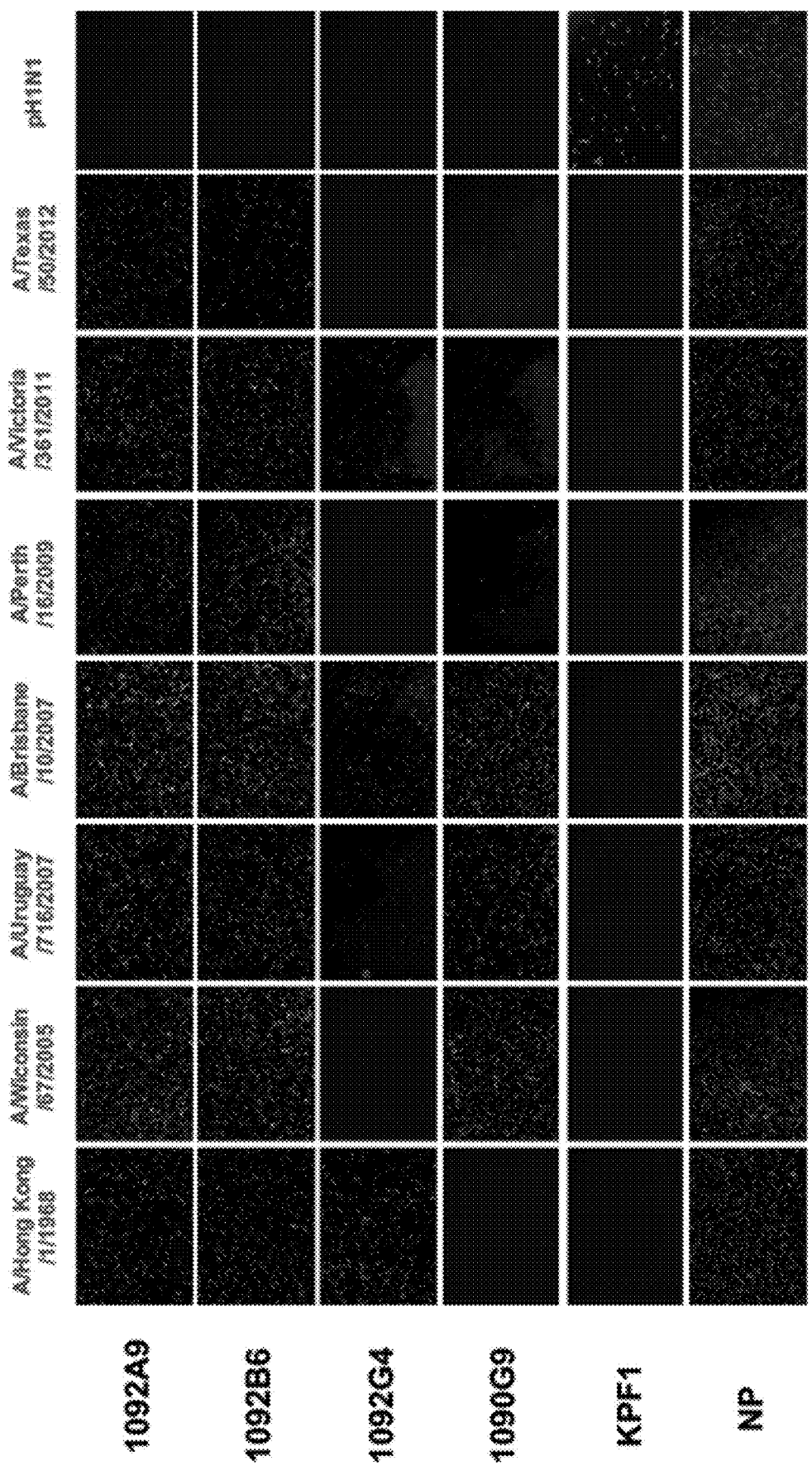
FIG. 7 is a set of photographs showing that MDCK cells were mock infected (Mock) or infected with the indicated viruses and later were fixed and stained with 1 µg/ml of the NA-specific hMAbs and NA protein expression evaluated by IFA. KPF1 is an H1-specific hMAb used as an internal control in this IFA.

Assays similar to those described in Example 5 above were carried out to examine the above-described N2-specific mAbs: 1092A9, 1092B6, 1092G4, and 1090G9. The results are shown in FIG. 7. Briefly, MDCK cells were mock infected or infected with the indicated viruses and later were fixed and stained with 1 µg/ml of the NA-specific hMAbs and NA protein expression evaluated by IFA. KPF1 is an H1-specific hMAb used as an internal control in this IFA. The results indicate increased breadth of mAbs to bind to multiple H3N2 viruses.

Figures 8A, 8B, 8C:
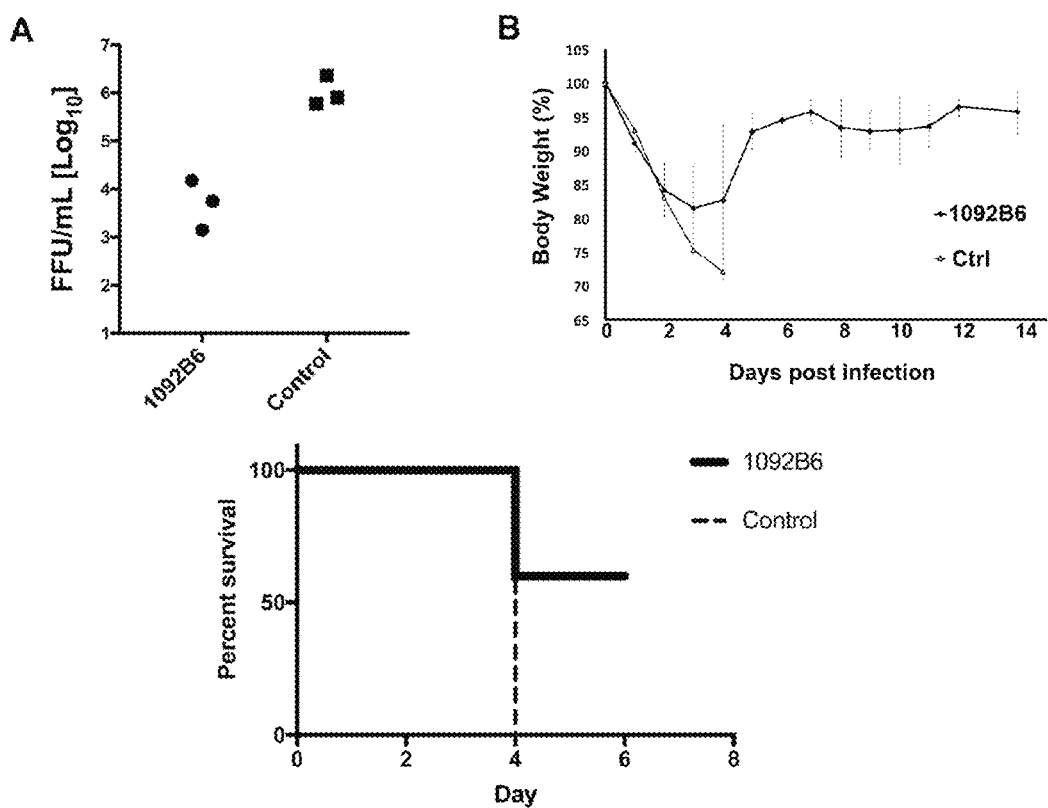
FIGS. 8A, 8B, and 8C are a set of diagrams showing in vivo prophylactic activity of the 1092B6 N2 hmAb. Female C57BL/6 mice were administered the 1092B6 or isotype control hmAb at 20 mg/kg intraperitoneally (i.p.). At 6 h after dosing, mice were inoculated intranasally (i.n.) with $1 \times 10^6$ focus-forming units (FFU) X31 influenza virus. (A) Viral replication was determined by measuring viral titers in the lungs of the infected mice at 4 days post infection (n=3 mice per group). Body weight (B) and survival (C) was monitored (n=5 mice per group).

Assays similar to those described in Example 6 above were carried out to examine the in vivo prophylactic activity of the 1092B6 N2 hmAb. The results are shown in FIGS. 8A, 8B and 8C. The result shows ability of 1092B6 to reduce viral burden and increase survival in H3N2 infected mice.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

What is claimed is:

1. An isolated antibody or antigen-binding fragment thereof that specifically binds to a neuraminidase of influenza virus, comprising:
   (i) a heavy chain variable region that comprises HCDR1, HCDR2, and HCDR3 comprising the respective sequences of SEQ ID NOs: 43-45, and
   (ii) a light chain variable region that comprises LCDR1, LCDR2, and LCDR3 comprising the respective sequences of SEQ ID NOs: 46-48.

2. The isolated antibody or the antigen-binding fragment thereof of claim 1, wherein
   the heavy chain variable region comprises the sequence of SEQ ID NO: 41 and the light chain variable region comprises the sequence of SEQ ID NO: 42.

3. The isolated antibody or the antigen-binding fragment thereof of claim 1, further comprising a variant Fc constant region.

4. The isolated antibody or the antigen-binding fragment thereof of claim 1, wherein the antibody is a chimeric antibody, a humanized antibody, or a human antibody.

5. The isolated antibody or the antigen-binding fragment thereof of claim 1, wherein the antibody or fragment is conjugated to a therapeutic agent, a polymer, a detectable label, or an enzyme.

6. The isolated antibody or the antigen-binding fragment thereof of claim 5, wherein the polymer is polyethylene glycol (PEG).

7. The isolated antibody or the antigen-binding fragment thereof of claim 5, wherein the therapeutic agent is cytotoxic agent.

8. An isolated nucleic acid encoding the heavy or light chain variable region of the antibody, or antigen binding portion thereof, of claim 1.

9. An expression vector comprising the nucleic acid of claim 8.

10. A cultured host cell comprising the expression vector of claim 9.

11. A method of preparing an antibody, or antigen-binding portion thereof, comprising: obtaining a cultured host cell comprising a vector comprising a nucleic acid sequence encoding a CDR, a heavy chain variable region, or a light chain variable region of the antibody or antigen binding portion thereof of claim 1;
   culturing the cell in a medium under conditions permitting expression of a polypeptide encoded by the vector and assembling of an antibody or fragment thereof, and
   purifying the antibody or fragment from the cultured cell or the medium of the cell.

12. A pharmaceutical composition comprising the antibody or the antigen-binding fragment thereof of claim 1 and a pharmaceutically acceptable carrier.

13. A method of neutralizing influenza virus in a subject comprising administering to the subject a therapeutically effective amount of the antibody or the antigen-binding fragment thereof of claim 1.

14. The method of claim 13, further comprising administering to the subject a therapeutically effective amount of a second antibody or an antigen-binding fragment thereof.

15. A method of treating an influenza virus infection comprising administering to a subject in need thereof therapeutically effective amount of the antibody or the antigen-binding fragment thereof of claim 1.

16. The method of claim 15, further comprising administering to the subject a therapeutically effective amount of a second antibody or an antigen-binding fragment thereof.

* * * * *

```
                              SEQUENCE LISTING

Sequence total quantity: 75
SEQ ID NO: 1              moltype = AA  length = 121
FEATURE                   Location/Qualifiers
REGION                    1..121
                          note = recombinant
source                    1..121
                          mol_type = protein
                          organism = synthetic construct
SEQUENCE: 1
EVQLLQSGGG LVQPGGSLRL SCAASGLTFS GYAMSWVRQV PGKGPECVSG IIASGGSTYF    60
ADSVKGRFTI SRDNSKNTLD LEMNSLRAED TAVYYCAQHT KSHYYSGMGV WGQGTTVTVS   120
S                                                                   121

SEQ ID NO: 2              moltype = AA  length = 107
FEATURE                   Location/Qualifiers
REGION                    1..107
                          note = recombinant
source                    1..107
                          mol_type = protein
                          organism = synthetic construct
SEQUENCE: 2
DIQMTQSPSS LSASVGDRVT ITCQASQDIS NYLNWYQQRP GKAPKLLIYD AANLETGVPS    60
RFSGSGSATQ FTFTISGLQP EDFATYYCQQ YDNLPLTFGG GTKVEIK                 107

SEQ ID NO: 3              moltype = AA  length = 8
FEATURE                   Location/Qualifiers
REGION                    1..8
                          note = recombinant
source                    1..8
                          mol_type = protein
                          organism = synthetic construct
SEQUENCE: 3
GLTFSGYA                                                              8

SEQ ID NO: 4              moltype = AA  length = 8
FEATURE                   Location/Qualifiers
REGION                    1..8
                          note = recombinant
source                    1..8
                          mol_type = protein
                          organism = synthetic construct
SEQUENCE: 4
IIASGGST                                                              8

SEQ ID NO: 5              moltype = AA  length = 14
FEATURE                   Location/Qualifiers
REGION                    1..14
                          note = recombinant
source                    1..14
                          mol_type = protein
                          organism = synthetic construct
SEQUENCE: 5
AQHTKSHYYS GMGV                                                      14

SEQ ID NO: 6              moltype = AA  length = 6
FEATURE                   Location/Qualifiers
REGION                    1..6
                          note = recombinant
source                    1..6
                          mol_type = protein
                          organism = synthetic construct
SEQUENCE: 6
QDISNY                                                                6

SEQ ID NO: 7              moltype =     length =
SEQUENCE: 7
000

SEQ ID NO: 8              moltype = AA  length = 9
```

```
FEATURE                 Location/Qualifiers
REGION                  1..9
                        note = recombinant
source                  1..9
                        mol_type = protein
                        organism = synthetic construct
SEQUENCE: 8
QQYDNLPLT                                                                  9

SEQ ID NO: 9            moltype = AA  length = 124
FEATURE                 Location/Qualifiers
REGION                  1..124
                        note = recombinant
source                  1..124
                        mol_type = protein
                        organism = synthetic construct
SEQUENCE: 9
QVQLVQSGAE VRKPGASVKV SCKVSRYNII ELSMDWVRQA PGKGLEWMGG IDPDDSERIY          60
AQKLQGRVTM TEDTSTDTAY MELSGLRSED TAIYYCAAAR RPIRGEYHYA LDVWGQGTAV         120
TVSS                                                                     124

SEQ ID NO: 10           moltype = AA  length = 105
FEATURE                 Location/Qualifiers
REGION                  1..105
                        note = recombinant
source                  1..105
                        mol_type = protein
                        organism = synthetic construct
SEQUENCE: 10
EIVLTQSPGT LSLSPGERAT LSCRASQSVS SSYLGWYQQK PGQAPRLLIY RASSRATGIP          60
HRFSGSGSGT EFTLTITRLE PEDFAVYYCH HYAKVFGQGT KVEIK                         105

SEQ ID NO: 11           moltype = AA  length = 8
FEATURE                 Location/Qualifiers
REGION                  1..8
                        note = recombinant
source                  1..8
                        mol_type = protein
                        organism = synthetic construct
SEQUENCE: 11
RYNIIELS                                                                   8

SEQ ID NO: 12           moltype = AA  length = 8
FEATURE                 Location/Qualifiers
REGION                  1..8
                        note = recombinant
source                  1..8
                        mol_type = protein
                        organism = synthetic construct
SEQUENCE: 12
IDPDDSER                                                                   8

SEQ ID NO: 13           moltype = AA  length = 17
FEATURE                 Location/Qualifiers
REGION                  1..17
                        note = recombinant
source                  1..17
                        mol_type = protein
                        organism = synthetic construct
SEQUENCE: 13
AAARRPIRGE YHYALDV                                                        17

SEQ ID NO: 14           moltype = AA  length = 7
FEATURE                 Location/Qualifiers
REGION                  1..7
                        note = recombinant
source                  1..7
                        mol_type = protein
                        organism = synthetic construct
SEQUENCE: 14
QSVSSSY                                                                    7

SEQ ID NO: 15           moltype =     length =
SEQUENCE: 15
000

SEQ ID NO: 16           moltype = AA  length = 6
FEATURE                 Location/Qualifiers
REGION                  1..6
```

```
                            note = recombinant
source                      1..6
                            mol_type = protein
                            organism = synthetic construct
SEQUENCE: 16
HHYAKV                                                                        6

SEQ ID NO: 17               moltype = AA  length = 124
FEATURE                     Location/Qualifiers
REGION                      1..124
                            note = recombinant
source                      1..124
                            mol_type = protein
                            organism = synthetic construct
SEQUENCE: 17
QVQLVQSGAD VKKPGASVKV SCKVSGYSLT ELSMHWVRQA PGKGLEWMGG LDPDNGEIIY           60
AQKFQGRVAM TEDTSTDTAY MELSSLRSED TALYYCAAAR RPIRGEYHYG MDVWGQGTTV          120
TVSS                                                                      124

SEQ ID NO: 18               moltype = AA  length = 105
FEATURE                     Location/Qualifiers
REGION                      1..105
                            note = recombinant
source                      1..105
                            mol_type = protein
                            organism = synthetic construct
SEQUENCE: 18
EIVLTQSPGT LSLSPGERAT LSCRASQSLS SSYLAWYQQK SGQAPRLLIY GASSRATGVP           60
DRFSGSGSGT DFTLTISRLE PEDFAVYYCQ QYGKAFGQGT KVEIK                          105

SEQ ID NO: 19               moltype = AA  length = 8
FEATURE                     Location/Qualifiers
REGION                      1..8
                            note = recombinant
source                      1..8
                            mol_type = protein
                            organism = synthetic construct
SEQUENCE: 19
GYSLTELS                                                                      8

SEQ ID NO: 20               moltype = AA  length = 8
FEATURE                     Location/Qualifiers
REGION                      1..8
                            note = recombinant
source                      1..8
                            mol_type = protein
                            organism = synthetic construct
SEQUENCE: 20
LDPDNGEI                                                                      8

SEQ ID NO: 21               moltype = AA  length = 17
FEATURE                     Location/Qualifiers
REGION                      1..17
                            note = recombinant
source                      1..17
                            mol_type = protein
                            organism = synthetic construct
SEQUENCE: 21
AAARRPIRGE YHYGMDV                                                           17

SEQ ID NO: 22               moltype = AA  length = 7
FEATURE                     Location/Qualifiers
REGION                      1..7
                            note = recombinant
source                      1..7
                            mol_type = protein
                            organism = synthetic construct
SEQUENCE: 22
QSLSSSY                                                                       7

SEQ ID NO: 23               moltype =   length =
SEQUENCE: 23
000

SEQ ID NO: 24               moltype = AA  length = 6
FEATURE                     Location/Qualifiers
REGION                      1..6
                            note = recombinant
source                      1..6
```

```
SEQUENCE: 24
QQYGKA                                                                      6

SEQ ID NO: 25           moltype = AA  length = 127
FEATURE                 Location/Qualifiers
REGION                  1..127
                        note = recombinant
source                  1..127
                        mol_type = protein
                        organism = synthetic construct
SEQUENCE: 25
EVQLLESGGQ LVQPGGSLRL SCAVSGFTFS RYAMYWVRQA PGKGLEWVSI ISGDGGVTFY           60
ADSVKGRFTI SRDNSKNTLF LQMNSLRADD TAVYYCAKDN QDLDLWSGSY KGTFDDWGQG          120
TLVTVSS                                                                   127

SEQ ID NO: 26           moltype = AA  length = 111
FEATURE                 Location/Qualifiers
REGION                  1..111
                        note = recombinant
source                  1..111
                        mol_type = protein
                        organism = synthetic construct
SEQUENCE: 26
NFMLTQPHSV SGSPGKTVSI SCTRSSGIIA SNHVQWYQQR PGSAPTTVIF EDNQRPSGVP           60
DRFSGSIDSS SNSASLTISG LKTEDEADYY CQSYDSSRYW VFGGGTKLTV L                  111

SEQ ID NO: 27           moltype = AA  length = 8
FEATURE                 Location/Qualifiers
REGION                  1..8
                        note = recombinant
source                  1..8
                        mol_type = protein
                        organism = synthetic construct
SEQUENCE: 27
GFTFSRYA                                                                    8

SEQ ID NO: 28           moltype = AA  length = 8
FEATURE                 Location/Qualifiers
REGION                  1..8
                        note = recombinant
source                  1..8
                        mol_type = protein
                        organism = synthetic construct
SEQUENCE: 28
ISGDGGVT                                                                    8

SEQ ID NO: 29           moltype = AA  length = 20
FEATURE                 Location/Qualifiers
REGION                  1..20
                        note = recombinant
source                  1..20
                        mol_type = protein
                        organism = synthetic construct
SEQUENCE: 29
AKDNQDLDLW SGSYKGTFDD                                                      20

SEQ ID NO: 30           moltype = AA  length = 8
FEATURE                 Location/Qualifiers
REGION                  1..8
                        note = recombinant
source                  1..8
                        mol_type = protein
                        organism = synthetic construct
SEQUENCE: 30
SGIIASNH                                                                    8

SEQ ID NO: 31           moltype =     length =
SEQUENCE: 31
000

SEQ ID NO: 32           moltype = AA  length = 10
FEATURE                 Location/Qualifiers
REGION                  1..10
                        note = recombinant
source                  1..10
                        mol_type = protein
                        organism = synthetic construct
```

```
SEQUENCE: 32
QSYDSSRYWV                                                              10

SEQ ID NO: 33           moltype = AA  length = 123
FEATURE                 Location/Qualifiers
REGION                  1..123
                        note = recombinant
source                  1..123
                        mol_type = protein
                        organism = synthetic construct
SEQUENCE: 33
VQLVESGGGV VQPGRSLRLS CVASGFSLST YGMLWVRQAP GKGLVWVALI SYEEGSNKKY        60
ADSVKGRFTI SRDNSRNTLY LQMSSLTSDD TGVYYCARDA GCDSVGYYPG RLWGQGTLVT       120
VSS                                                                    123

SEQ ID NO: 34           moltype = AA  length = 111
FEATURE                 Location/Qualifiers
REGION                  1..111
                        note = recombinant
source                  1..111
                        mol_type = protein
                        organism = synthetic construct
SEQUENCE: 34
QSVLTQPPSA SGTPGQTVTI SCSGTSSNIG SNFVYWYQQL PGTAPKLLIF RNNQRPSGVP        60
DRFSGSKSGT SASLAVSGLR SEDEAEYYCA AWDDSLSGHL VFGGGTKLTV L                111

SEQ ID NO: 35           moltype = AA  length = 8
FEATURE                 Location/Qualifiers
REGION                  1..8
                        note = recombinant
source                  1..8
                        mol_type = protein
                        organism = synthetic construct
SEQUENCE: 35
GFSLSTYG                                                                 8

SEQ ID NO: 36           moltype = AA  length = 9
FEATURE                 Location/Qualifiers
REGION                  1..9
                        note = recombinant
source                  1..9
                        mol_type = protein
                        organism = synthetic construct
SEQUENCE: 36
ISYEEGSNK                                                                9

SEQ ID NO: 37           moltype = AA  length = 16
FEATURE                 Location/Qualifiers
REGION                  1..16
                        note = recombinant
source                  1..16
                        mol_type = protein
                        organism = synthetic construct
SEQUENCE: 37
ARDAGCDSVG YYPGRL                                                       16

SEQ ID NO: 38           moltype = AA  length = 8
FEATURE                 Location/Qualifiers
REGION                  1..8
                        note = recombinant
source                  1..8
                        mol_type = protein
                        organism = synthetic construct
SEQUENCE: 38
SSNIGSNF                                                                 8

SEQ ID NO: 39           moltype =     length =
SEQUENCE: 39
000

SEQ ID NO: 40           moltype = AA  length = 12
FEATURE                 Location/Qualifiers
REGION                  1..12
                        note = recombinant
source                  1..12
                        mol_type = protein
                        organism = synthetic construct
SEQUENCE: 40
AAWDDSLSGH LV                                                           12
```

```
SEQ ID NO: 41           moltype = AA  length = 122
FEATURE                 Location/Qualifiers
REGION                  1..122
                        note = recombinant
source                  1..122
                        mol_type = protein
                        organism = synthetic construct
SEQUENCE: 41
VQLVESGGGV VQPGRSLRLS CAASGFTFNT HPMHWVRQAP GKGLDWVAVI SYDGSDEYYA   60
DSVKGRFTIS RDDSKNTLYL QMNSLRPEDT AIYYCARDAG YDSRGYLPGP YWGQGTLVTV  120
SS                                                                122

SEQ ID NO: 42           moltype = AA  length = 111
FEATURE                 Location/Qualifiers
REGION                  1..111
                        note = recombinant
SITE                    105
                        note = misc_feature - Xaa can be any naturally occurring
                         amino acid
source                  1..111
                        mol_type = protein
                        organism = synthetic construct
SEQUENCE: 42
QSVLTQPPSA SGTPGQTVTI SCSGSASTIG NNYVYWYQQL PGMAPKLLIF RDNQRPSRVP   60
DRFSGSKSGT SASLAIRGVR SDDEADYYCA AWDDSLSGHV MFGGXTKLTV L           111

SEQ ID NO: 43           moltype = AA  length = 8
FEATURE                 Location/Qualifiers
REGION                  1..8
                        note = recombinant
source                  1..8
                        mol_type = protein
                        organism = synthetic construct
SEQUENCE: 43
GFTFNTHP                                                            8

SEQ ID NO: 44           moltype = AA  length = 8
FEATURE                 Location/Qualifiers
REGION                  1..8
                        note = recombinant
source                  1..8
                        mol_type = protein
                        organism = synthetic construct
SEQUENCE: 44
ISYDGSDE                                                            8

SEQ ID NO: 45           moltype = AA  length = 16
FEATURE                 Location/Qualifiers
REGION                  1..16
                        note = recombinant
source                  1..16
                        mol_type = protein
                        organism = synthetic construct
SEQUENCE: 45
ARDAGYDSRG YLPGPY                                                  16

SEQ ID NO: 46           moltype = AA  length = 8
FEATURE                 Location/Qualifiers
REGION                  1..8
                        note = recombinant
source                  1..8
                        mol_type = protein
                        organism = synthetic construct
SEQUENCE: 46
ASTIGNNY                                                            8

SEQ ID NO: 47           moltype =     length =
SEQUENCE: 47
000

SEQ ID NO: 48           moltype = AA  length = 12
FEATURE                 Location/Qualifiers
REGION                  1..12
                        note = recombinant
source                  1..12
                        mol_type = protein
                        organism = synthetic construct
SEQUENCE: 48
```

```
AAWDDSLSGH VM                                                           12

SEQ ID NO: 49           moltype = AA  length = 131
FEATURE                 Location/Qualifiers
REGION                  1..131
                        note = recombinant
source                  1..131
                        mol_type = protein
                        organism = synthetic construct
SEQUENCE: 49
EVQLVESGGG SVKPGGSLRL SCAASGFTFT NSWMSWVRQA PGKGLEWVGR IKSKSDGTT        60
DYAAPVKGRF SISRDDSKST LFLQMNSLKT EDTAVYYCSA APFTESNGYK SWDYLYGMDV       120
WGQGTTVTVS S                                                            131

SEQ ID NO: 50           moltype = AA  length = 106
FEATURE                 Location/Qualifiers
REGION                  1..106
                        note = recombinant
source                  1..106
                        mol_type = protein
                        organism = synthetic construct
SEQUENCE: 50
SYELTQPPSV SVSPGQTATI TCSGDKLGDK FASWYQQQPG QSPVLVIYQH TKRPSGIPER        60
FSGSISGSTA TLTISGTQAV DEADYYCQAW DSNSYVFGAG TKVTVL                       106

SEQ ID NO: 51           moltype = AA  length = 8
FEATURE                 Location/Qualifiers
REGION                  1..8
                        note = recombinant
source                  1..8
                        mol_type = protein
                        organism = synthetic construct
SEQUENCE: 51
GFTFTNSW                                                                 8

SEQ ID NO: 52           moltype = AA  length = 9
FEATURE                 Location/Qualifiers
REGION                  1..9
                        note = recombinant
source                  1..9
                        mol_type = protein
                        organism = synthetic construct
SEQUENCE: 52
KSKSDGGTT                                                                9

SEQ ID NO: 53           moltype = AA  length = 22
FEATURE                 Location/Qualifiers
REGION                  1..22
                        note = recombinant
source                  1..22
                        mol_type = protein
                        organism = synthetic construct
SEQUENCE: 53
SAAPFTESNG YKSWDYLYGM DV                                                 22

SEQ ID NO: 54           moltype = AA  length = 6
FEATURE                 Location/Qualifiers
REGION                  1..6
                        note = recombinant
source                  1..6
                        mol_type = protein
                        organism = synthetic construct
SEQUENCE: 54
KLGDKF                                                                   6

SEQ ID NO: 55           moltype =    length =
SEQUENCE: 55
000

SEQ ID NO: 56           moltype = AA  length = 9
FEATURE                 Location/Qualifiers
REGION                  1..9
                        note = recombinant
source                  1..9
                        mol_type = protein
                        organism = synthetic construct
SEQUENCE: 56
QAWDSNSYV                                                                9
```

```
SEQ ID NO: 57              moltype = AA   length = 123
FEATURE                    Location/Qualifiers
REGION                     1..123
                           note = recombinant
source                     1..123
                           mol_type = protein
                           organism = synthetic construct
SEQUENCE: 57
QVQLQESGPG LVKPSETLSL TCTVSGGSIS SYYWSWIRQP PGKAVEWIGY IFDGGSTDYN    60
PSLKSRVAMS VDASENQFSL KLASVTAADT AVYYCARYRV SGNYYDTPWF DPWGQGLLVT   120
VSS                                                                 123

SEQ ID NO: 58              moltype = AA   length = 108
FEATURE                    Location/Qualifiers
REGION                     1..108
                           note = recombinant
source                     1..108
                           mol_type = protein
                           organism = synthetic construct
SEQUENCE: 58
SYELTQPPSL SASPGQTARI TCSGDALPKQ DVYWYQQKPG QAPLLVIYKD TERPSGIPER    60
FSGSRSGTTV TLIISGVQAE DEADYYCQSA ASSYGYVVFG GGTKLTVL                108

SEQ ID NO: 59              moltype = AA   length = 8
FEATURE                    Location/Qualifiers
REGION                     1..8
                           note = recombinant
source                     1..8
                           mol_type = protein
                           organism = synthetic construct
SEQUENCE: 59
GGSISSYY                                                              8

SEQ ID NO: 60              moltype = AA   length = 7
FEATURE                    Location/Qualifiers
REGION                     1..7
                           note = recombinant
source                     1..7
                           mol_type = protein
                           organism = synthetic construct
SEQUENCE: 60
IFDGGST                                                               7

SEQ ID NO: 61              moltype = AA   length = 17
FEATURE                    Location/Qualifiers
REGION                     1..17
                           note = recombinant
source                     1..17
                           mol_type = protein
                           organism = synthetic construct
SEQUENCE: 61
ARYRVSGNYY DTPWFDP                                                   17

SEQ ID NO: 62              moltype = AA   length = 6
FEATURE                    Location/Qualifiers
REGION                     1..6
                           note = recombinant
source                     1..6
                           mol_type = protein
                           organism = synthetic construct
SEQUENCE: 62
ALPKQD                                                                6

SEQ ID NO: 63              moltype =     length =
SEQUENCE: 63
000

SEQ ID NO: 64              moltype = AA   length = 11
FEATURE                    Location/Qualifiers
REGION                     1..11
                           note = recombinant
source                     1..11
                           mol_type = protein
                           organism = synthetic construct
SEQUENCE: 64
QSAASSYGYV V                                                         11

SEQ ID NO: 65              moltype = AA   length = 127
FEATURE                    Location/Qualifiers
```

```
REGION                  1..127
                        note = recombinant
source                  1..127
                        mol_type = protein
                        organism = synthetic construct
SEQUENCE: 65
EVQLLESGGQ LVQPGGSLRL SCAVSGFTFS SYAMYWVRQS PGKGLEWVSI ISGDGGVTFY    60
ADSVKGRFTI SRDNSKNTLY LQMNSLRAED TAVYYCAKDK QDLDLWSGSY KGTFDEWGQG   120
TLVTVSS                                                             127

SEQ ID NO: 66           moltype = AA  length = 111
FEATURE                 Location/Qualifiers
REGION                  1..111
                        note = recombinant
source                  1..111
                        mol_type = protein
                        organism = synthetic construct
SEQUENCE: 66
NFMLTQPHSV SGSPGKTVSI SCTRSSGIIA SNYVQWYQQR PGSAPTTVIF EDNQRPSGVP    60
DRFSGSIDSS SNSASLTISG LKTEDEADYY CQSYDSSRYW VFGGGTKLTV L            111

SEQ ID NO: 67           moltype = AA  length = 8
FEATURE                 Location/Qualifiers
REGION                  1..8
                        note = recombinant
source                  1..8
                        mol_type = protein
                        organism = synthetic construct
SEQUENCE: 67
GFTFSSYA                                                              8

SEQ ID NO: 68           moltype = AA  length = 8
FEATURE                 Location/Qualifiers
REGION                  1..8
                        note = recombinant
source                  1..8
                        mol_type = protein
                        organism = synthetic construct
SEQUENCE: 68
ISGDGGVT                                                              8

SEQ ID NO: 69           moltype = AA  length = 20
FEATURE                 Location/Qualifiers
REGION                  1..20
                        note = recombinant
source                  1..20
                        mol_type = protein
                        organism = synthetic construct
SEQUENCE: 69
AKDKQDLDLW SGSYKGTFDE                                                20

SEQ ID NO: 70           moltype = AA  length = 8
FEATURE                 Location/Qualifiers
REGION                  1..8
                        note = recombinant
source                  1..8
                        mol_type = protein
                        organism = synthetic construct
SEQUENCE: 70
SGIIASNY                                                              8

SEQ ID NO: 71           moltype =    length =
SEQUENCE: 71
000

SEQ ID NO: 72           moltype = AA  length = 10
FEATURE                 Location/Qualifiers
REGION                  1..10
                        note = recombinant
source                  1..10
                        mol_type = protein
                        organism = synthetic construct
SEQUENCE: 72
QSYDSSRYWV                                                           10

SEQ ID NO: 73           moltype = AA  length = 9
FEATURE                 Location/Qualifiers
source                  1..9
                        mol_type = protein
```

```
                        organism = Influenza virus
SEQUENCE: 73
ILRTQESEC                                                                    9

SEQ ID NO: 74           moltype = DNA  length = 17
FEATURE                 Location/Qualifiers
misc_feature            1..17
                        note = primer
source                  1..17
                        mol_type = other DNA
                        organism = synthetic construct
SEQUENCE: 74
taaraggtgt ccagtgt                                                          17

SEQ ID NO: 75           moltype = DNA  length = 20
FEATURE                 Location/Qualifiers
misc_feature            1..20
                        note = primer
source                  1..20
                        mol_type = other DNA
                        organism = synthetic construct
SEQUENCE: 75
agtttgggct gagctggctt                                                       20
```